US012747437B2

(12) United States Patent
Yasui et al.

(10) Patent No.: US 12,747,437 B2
(45) Date of Patent: Sep. 29, 2026

(54) BIOMOLECULE EXTRACTION METHOD

(71) Applicant: CRAIF INC., Tokyo (JP)

(72) Inventors: Takao Yasui, Nagoya (JP); Yoshinobu Baba, Nagoya (JP); Wataru Shinoda, Nagoya (JP); Atsushi Natsume, Nagoya (JP)

(73) Assignee: CRAIF INC., Tokyo (JP)

( * ) Notice: Subject to any disclaimer, the term of this patent is extended or adjusted under 35 U.S.C. 154(b) by 777 days.

(21) Appl. No.: 18/245,743

(22) PCT Filed: Sep. 17, 2021

(86) PCT No.: PCT/JP2021/034207

§ 371 (c)(1),
(2) Date: Mar. 17, 2023

(87) PCT Pub. No.: WO2022/059762

PCT Pub. Date: Mar. 24, 2022

(65) Prior Publication Data

US 2023/0357746 A1 Nov. 9, 2023

(30) Foreign Application Priority Data

Sep. 18, 2020 (JP) ................................ 2020-157294

(51) Int. Cl.
*C12N 15/10* (2006.01)
*C12Q 1/6806* (2018.01)

(52) U.S. Cl.
CPC ....... *C12N 15/1003* (2013.01); *C12Q 1/6806* (2013.01)

(58) Field of Classification Search
CPC .......................... C12N 15/1003; C12Q 1/6806
USPC ........................................................ 536/25.4
See application file for complete search history.

(56) References Cited

U.S. PATENT DOCUMENTS

| | | | |
|---|---|---|---|
| 2009/0061497 | A1 | 3/2009 | Collis et al. |
| 2017/0191054 | A1 | 7/2017 | Collis et al. |
| 2020/0255906 | A1 | 8/2020 | Yasui et al. |
| 2022/0033803 | A1 | 2/2022 | Yasui et al. |

FOREIGN PATENT DOCUMENTS

| | | | |
|---|---|---|---|
| JP | 2010-532483 | A | 10/2010 |
| JP | 2013-217699 | A | 10/2013 |
| JP | 2017-158484 | A | 9/2017 |
| JP | 2017-184626 | A | 10/2017 |
| JP | 2020-92688 | A | 6/2020 |
| JP | WO2020090860 | A1 | 10/2021 |
| KR | 10-2008-0028703 | A | 4/2008 |
| WO | 2015/137427 | A1 | 9/2015 |
| WO | 2017/221744 | A1 | 12/2017 |
| WO | 2020/054773 | A1 | 3/2020 |
| WO | 2020/090860 | A1 | 5/2020 |
| WO | 2020/158832 | A1 | 8/2020 |

OTHER PUBLICATIONS

Yasui et al. Unveiling massive numbers of cancer-related urinary-microRNA candidates via nanowires. Sci. Adv. 2017;3: e1701133. p. 1 of 19 to 19 of 19 (Dec. 15, 2017). Supplementary Materials: p. 20/31 to 31/31. (Year: 2017).*

Takahashi et al. Annealed ZnO/Al2O3 Core-Shell Nanowire as a Platform to Capture RNA in Blood Plasma. Nanomaterials 2021, 11, 1768. p. 1-9. https://doi.org/10.3390/nano11071768 (Published: Jul. 7, 2021). (Year: 2021).*

Machine English translation of Priority JP2020-157294, Sep. 18, 2020 (translated in Dec. 2025) (Year: 2025).*

International Search Report of International Patent Application No. PCT/JP2021/034207, mailed Nov. 22, 2021.

Yasui et al., "Unveiling massive Nos. of cancer-related urinary-microRNA candidates via nanowires", Science Advances, Dec. 15, 2017, pp. 1-19, vol. 3, No. 12.

* cited by examiner

*Primary Examiner* — Yih-Horng Shiao

(74) *Attorney, Agent, or Firm* — McBee, Moore & Vanik IP, LLC

(57) ABSTRACT

The present disclosure provides a method for extracting a biomolecule. The present disclosure provides a method for extracting a cell-free DNA. The present disclosure provides a method for concentrating a DNA having a non-base pairing base. The present disclosure provides a method for concentrating a DNA having a low methylation modification level.

15 Claims, 13 Drawing Sheets

FIG. 4A ZnO
FIG. 4B $ZnO/SiO_2$
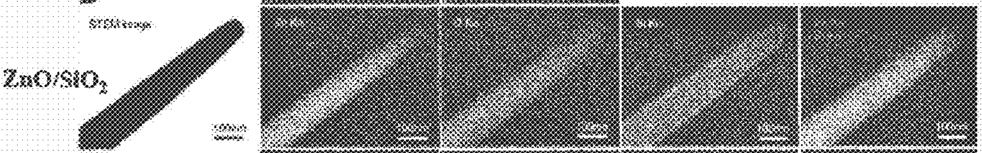
FIG. 4C $ZnO/Al_2O_3$
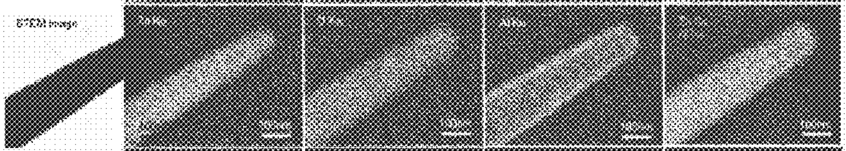
FIG. 4D $ZnO/TiO_2$
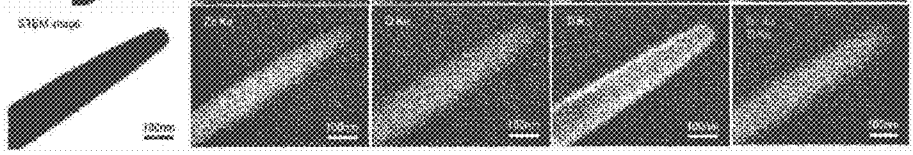
FIG. 5A
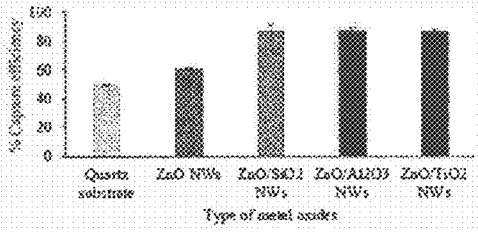
FIG. 5C
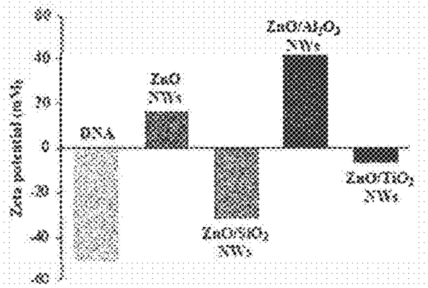
FIG. 5B
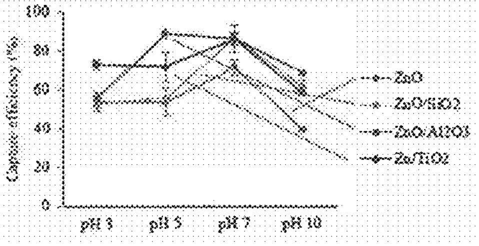

BIOMOLECULE EXTRACTION METHOD

CROSS-REFERENCE TO RELATED APPLICATIONS

This application is the National Stage entry of International Application No. PCT/JP2021/034207, filed 17 Sep. 2021, which claims priority to Japanese Application No. 2020-157294, filed 18 Sep. 2020.

REFERENCE TO SEQUENCE LISTING SUBMITTED AS A COMPLIANT ASCII TEXT FILE (.XML)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_3000068-009000_ST26" created on 12 Jan. 2023, and 43,046 bytes in size) is submitted concurrently with the instant application, and the entire contents of the Sequence Listing are incorporated herein by reference.

BACKGROUND

Field

The present disclosure relates to a method for extracting a biomolecule. The present disclosure relates to a method for extracting a cell-free DNA. The present disclosure also relates to a method for concentrating a DNA having a non-base pairing base. The present disclosure further relates to a method for concentrating a DNA having a low methylation modification level.

Description of Related Art

Attention has been focused on liquid biopsy, in which the health conditions of a subject are diagnosed using a body fluid, as a non-invasive high-accuracy test. A device and a method in which a body fluid is analyzed by capturing extracellular vesicles included in the body fluid on nanowires has been proposed (PTLs 1 to 4 and NPL 1). According to the above documents, extracellular vesicles, which include microRNAs, etc., can be captured with nanowires and the health conditions of a subject from which the body fluid is derived can be determined by analyzing the microRNAs included in the extracellular vesicles.

CITATION LIST

Patent Literature

PTL 1: US2020/0255906A
PTL 2: WO2015/137427A
PTL 3: WO2017/221744A
PTL 4: WO2020/054773A
PTL 5: JP2017-158484A

Non Patent Literature

NPL 1: T. Yasui et al., Science Advances, Vol. 3, no. 12, e1701133, 2017

SUMMARY

The present disclosure provides a method for extracting a biomolecule. The present disclosure provides a method for extracting a cell-free DNA. The present disclosure also provides a method for concentrating a DNA having a non-base pairing base. The present disclosure further provides a method for concentrating a DNA having a low methylation modification level.

According to the present disclosure, the following invention may be provided.

(1) A method for extracting a cell-free DNA (cfDNA) included in an aqueous solution, the method including:

bringing an oxide nanowire into contact with an aqueous solution including a cfDNA to cause the cfDNA to adsorb on the oxide nanowire.

(2) The method according to (1) above, wherein the cfDNA is single-stranded.

(3) The method according to (1) above, wherein the cfDNA is double-stranded.

(4) The method according to (3) above, wherein the cfDNA has a non-base pairing base.

(5) The method according to (4) above, wherein the cfDNA is a double-stranded DNA and has a non-base pairing base.

(6) The method according to any one of (1) to (5) above, wherein the aqueous solution includes a cfDNA having a first methylation level and a cfDNA having a second methylation level, the first methylation level is lower than the second methylation level, and the cfDNA having the first methylation level is concentrated.

(7) The method according to any one of (1) to (6) above, wherein the aqueous solution is a body fluid.

(8) The method according to (7) above, wherein the aqueous solution is urine.

(9) The method according to any one of (1) to (8) above, wherein the oxide is an oxide selected from the group consisting of zinc oxide, aluminum oxide, titanium oxide, and silicon oxide.

(10) The method according to any one of (1) to (9) above, wherein the adsorbed cfDNA is liberated using a solution selected from the group consisting of an ethylenediaminetetraacetic acid (EDTA)-containing aqueous solution, a low-salt strength aqueous solution, a heat treatment, and ethanol.

(11) A method including bringing a first oxide nanowire into contact with a portion of an aqueous solution including a first cfDNA to cause the first cfDNA to adsorb on the oxide nanowire, bringing a second oxide nanowire into contact with another portion of the aqueous solution including the first cfDNA to cause the first cfDNA to adsorb on the oxide nanowire, and comparing the amount of the first cfDNA adsorbed on the first oxide nanowire with the amount of the second cfDNA adsorbed on the second oxide wire to estimate the methylation level of the first cfDNA, wherein the first and second oxide wires are composed of different materials.

(12) A method including bringing a first oxide nanowire into contact with a portion of an aqueous solution including a first cfDNA to cause the first cfDNA to adsorb on the oxide nanowire, measuring the amount of the first cfDNA adsorbed, measuring the DNA amount of the first cfDNA present in another portion of the aqueous solution including the first cfDNA or the DNA concentration of the first cfDNA in the other portion of the aqueous solution including the first cfDNA (e.g., the measurement is conducted by sequencing or PCR (in particular, real-time PCR)), and estimating the methylation level of the first cfDNA on the basis of the content or concentration of the first cfDNA in the aqueous solution and the amount of the cfDNA adsorbed on the first oxide wire.

(13) The above-described method, further including converting a part or the entirety of the cfDNA into a single-stranded form before the oxide wire is brought into contact with the cfDNA.

BRIEF DESCRIPTION OF THE DRAWINGS

FIG. 4A-D illustrates the results of element mapping of various oxide nanowires prepared.

FIG. 5A-C illustrates the efficiencies with which the various oxide nanowires prepared captured cfDNAs, the impacts of pH on capture efficiency, and the zeta potentials of the oxide nanowires.

DETAILED DESCRIPTION OF A PREFERRED EMBODIMENT

Figure 1A:
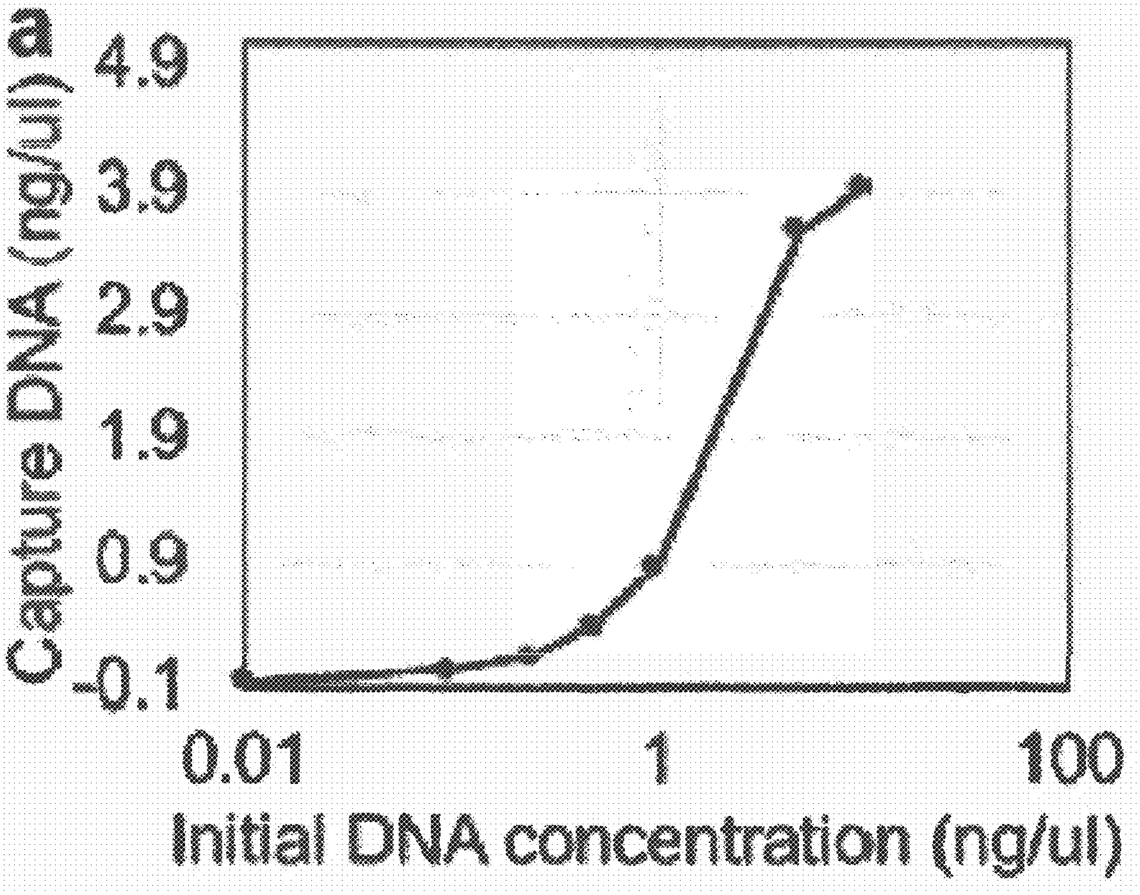
FIG. 1A illustrates the relationship between the concentration of cfDNAs brought into contact with nanowires and the amount of DNAs captured on the nanowires.

In the present specification, the term "target" refers to a subject whose body fluid is to be examined. The target may be an animal. The target may be a reptile, a mammal, or an amphibian. The mammal may be a dog, a cat, cattle, a horse, a sheep, a swine, a hamster, a rat, a mouse, a squirrel, or a primate, such as a monkey, a gorilla, a chimpanzee, a bonobo, or a human. In particular, the target may be a human.

In the present specification, the term "cell-free DNA" refers to a DNA that is present outside a cell. In the present specification, a cell-free DNA may also be referred to as "cfDNA". Cell-free DNAs may be included in a sample such as an aqueous solution. Examples of the sample include a sample obtained from the environment. Examples thereof include various types of samples that may include cfDNAs, such as environmental water samples taken from a river, a lake, a sea, a swamp, a paddy field, or groundwater and samples that do not contain moisture, such as soil, mud, and leaf soil. Examples of biological samples include samples taken from living bodies, such as a human, an animal, and a plant. Examples of the biological samples include body fluids (e.g., blood, an extratissue fluid, saliva, a lacrimal fluid, urine, sweat, and a secretory fluid). For example, a sample that includes cells may be used as a biological sample when cfDNAs are present outside the cells. In the present specification, the term "cell-free RNA" refers to an RNA present outside a cell, which may be a bare RNA or a free RNA. In the present specification, the term "free RNA" refers to an RNA that is not included in a cell or extracellular vesicle but is present in a solution in a bare and free form. An RNA (e.g., miRNA) may be a free RNA (e.g., miRNA).

In the present specification, the term "DNA" refers to a deoxyribonucleic acid, which may be single-stranded or double-stranded. In the present specification, the term "RNA" refers to a ribonucleic acid, which may be single-stranded or double-stranded. In the present specification, the term "ncRNA" refers to an RNA that does not code for proteins, which may be a miRNA.

A single-stranded DNA commonly has an exposed base (accessible base). The exposed base (accessible base) is commonly capable of pairing up with a counter base to form a Watson-Crick base pair (e.g., adenine (A) and thymine (T), that is, A-T base pair, or guanine (G) and cytosine (C), that is, G-C base pair). Examples of the single-stranded DNA include a DNA that does not have an intramolecular bond and a DNA that has an intramolecular bond. In a single-stranded DNA that does not have an intramolecular bond, the exposed base does not form a base pair in a free form. In the case where a complementary region is present in the molecule, a single-stranded DNA may have a base pair in the complementary region. Examples of the single-stranded DNA include a DNA that has a stem-hairpin structure. A DNA having a stem-hairpin structure includes a stem region in which the DNA is double-stranded and a single-stranded hairpin structure. The same applies to a single-stranded RNA.

A double-stranded DNA commonly has a base pair. The base pair forms a hydrogen bond between the two strands. Examples of the double-stranded DNA include a DNA having a blunt end and a DNA having a nonblunt end.

Examples of the DNA having a nonblunt end include a DNA in which a single-stranded base protrudes from one or both of the ends of a strand of the DNA (or from an end of a strand and the other end of the other strand).

Some embodiments of the present disclosure are described below with attention being focused on cfDNA. The term "cfDNA" can be read as a biomolecule, such as a cell, or a nucleic acid, such as an RNA (e.g., miRNA).

The cfDNAs may be subjected to methylation modification. The methylation modification of a DNA is performed on, for example, the cytosine of a CpG dinucleotide site. In a living body, the methylation of cytosine may be performed on the 5-position carbon atom of the pyrimidine ring.

An embodiment of the present disclosure provides a method for extracting (or detecting, concentrating, enriching, or purifying) a cell-free DNA (cfDNA) in an aqueous solution, the method including:

bringing an oxide nanowire into contact with an aqueous solution including a cfDNA to cause the cfDNA to adsorb on the oxide nanowire.

The above method may further include providing an aqueous solution including a cfDNA. The above method may further include washing away a component that has not adsorbed on the oxide nanowire. The above method may further include liberating the adsorbed cfDNA.

Another embodiment of the present disclosure provides a method for extracting (or detecting, concentrating, enriching, or purifying) a cell-free DNA (cfDNA) included in an aqueous solution, the method including:

providing an aqueous solution including a cfDNA;

bringing an oxide nanowire into contact with the aqueous solution including a cfDNA to cause the cfDNA to adsorb on the oxide nanowire;

washing away a component that has not adsorbed on the oxide nanowire; and liberating the adsorbed cfDNA.

(Providing Aqueous Solution Including cfDNA)

In an embodiment of the present disclosure, providing an aqueous solution including cfDNAs may include dispersing a sample including cfDNAs in an aqueous solution to dissolve or disperse the water-soluble cfDNAs in the aqueous solution. Providing an aqueous solution including cfDNAs may include obtaining an aqueous solution including cfDNAs by, after the above step, causing a solid component to settle and taking a supernatant including the cfDNAs dissolved therein. In the case where the sample is already an aqueous solution including cfDNAs, providing an aqueous solution including cfDNAs is to obtain the aqueous solution. The aqueous solution including cfDNAs may be a biological sample. The aqueous solution including cfDNAs may be, for example, a biological sample taken from a target. The aqueous solution including cfDNAs may be a sample that has been pretreated in order to make it easy to handle the sample. For example, in the case where the biological sample is blood, the pretreatment may be a treatment for obtaining serum or a treatment for obtaining plasma. The pretreatment may be, for example, a treatment for removing a solid component. The solid component can be separated from a solution component by centrifugation, filtering treatment, or the like. The pretreatment may include a treatment in which, for example, cfDNAs are separated, isolated, or concentrated from a sample.

The cfDNA may be a double-stranded DNA. The ends of the double-stranded DNA may be either blunt or nonblunt ends. Note that the interaction between a DNA and nanowires increases when the DNA includes a non-base pairing base. Therefore, a double-stranded DNA may be pretreated with a restriction enzyme that forms cohesive ends in order to form nonblunt ends. Thus, an aqueous solution including cfDNAs can be pretreated by adding a restriction enzyme or the like to an aqueous solution including double-stranded cfDNAs. Accordingly, this step may further include obtaining double-stranded DNAs having nonblunt ends by the above-described pretreatment. Alternatively, it may be prepared by adding a base to the 3'-terminal of a double-stranded cfDNA having blunt ends using an enzyme having a terminal deoxynucleotidyl transferase (TdT) activity (e.g., DNA polymerase). The blunt ends can be formed by DNA ultrasonication, a treatment using a restriction enzyme that produces blunt ends, a T4 DNA polymerase treatment, or the like.

In the case where the cfDNAs include a methylation-modified base, the cfDNAs may be pretreated with a Type-IV restriction enzyme. This enables the DNAs to be fragmented in a methylation-modification-dependent manner. The fragmentation may reduce the binding affinity to nanowires.

(Bringing Oxide Nanowire into Contact with Aqueous Solution Including cfDNA to Cause cfDNA to Adsorb on Oxide Nanowire)

According to an embodiment of the present disclosure, a single-stranded DNA has a non-base pairing base, and the oxide nanowires and the base may interact with each other through hydrogen bonds. According to an embodiment of the present disclosure, a double-stranded DNA may interact with the oxide nanowires even when it does not have a non-base pairing base, and the interaction may occur between the phosphate backbone of the DNA and the oxide nanowires. The above hydrogen bonds may include water molecules interposed therebetween. Specifically, the oxygen atoms included in the oxide nanowires interact with the hydrogen atoms included in the water molecules, and the oxygen atoms included in the water molecules interact with the non-base pairing bases of DNAs by hydrogen bonding. The above interaction is strong and may be stronger than the interaction between the phosphate backbone and the oxide nanowires.

Thus, as oxide nanowires, nanowires having a surface composed of an oxide can be used. The cores of the wires may be composed of any material as long as the surfaces of the wires are composed of an oxide. In an aspect, the surfaces and core wires may be composed of an oxide (e.g., a metal oxide, such as zinc oxide). The above oxide may be silicon oxide or a metal oxide. The metal oxide may be a metal oxide selected from the group consisting of platinum oxide, copper oxide, cobalt oxide, silver oxide, tin oxide, indium oxide, gallium oxide, chromium oxide, zinc oxide, aluminum oxide, nickel oxide, and titanium oxide. Since oxygen has the highest electronegativity after F, all oxides and metal oxides are useful as a material for the nanowires. In an aspect, the oxide may be an oxide of an atom having an electronegativity of 2.5 or less, 2.4 or less, 2.3 or less, 2.2 or less, 2.1 or less, 2.0 or less, 1.9 or less, 1.8 or less, 1.7 or less, or 1.6 or less. In an aspect, the nanowires have a positive zeta potential. In an aspect, the nanowires have a negative zeta potential.

In an aspect, the first oxide wire has a surface composed of ZnO, and the second oxide nanowire has a surface composed of any selected from the group consisting of $TiO_2$, $Al_2O_3$, and $SiO_2$.

The oxide nanowires and the aqueous solution including cfDNAs can be brought into contact with each other using a microfluidic device. Examples of the microfluidic device include the microfluidic devices described in US2020/

0255906A, WO2015/137427A, and JP2017-158484A. The microfluidic device has a channel. The channel may include a chaotic mixer. The microfluidic device includes nanowires disposed in the channel. The number of the nanowires may be two or more, and the microfluidic device may include a large number of nanowires. The microfluidic device may include a region in which a dense cluster of nanowires are present. When cfDNAs are brought into contact with the oxide nanowires, they may adsorb on the nanowires.

The adsorption is performed under conditions suitable for DNAs adsorbing on the nanowires. For DNAs adsorbing on the nanowires, it is necessary that the solution conditions and the like be suitable for the adsorption. The adsorption is performed for a certain period of time sufficient for DNAs to adsorb on the nanowires.

cfDNAs may adsorb on the oxide nanowires in a preferred manner. In particular, single-stranded cfDNAs having a length of 1 base pair or more, preferably having a length of 2 base pairs or more, and more preferably having a length of 3 base pairs or more are capable of adsorbing on the oxide nanowires in an advantageous manner. The longer a cfDNA is, the higher the binding affinity to the oxide nanowires may be. The length of the cfDNAs may be, for example, 5 base pairs or more, 10 base pairs or more, 20 base pairs or more, 30 base pairs or more, 40 base pairs or more, 50 base pairs or more, 60 base pairs or more, 70 base pairs or more, 80 base pairs or more, 90 base pairs or more, or 100 base pairs or more.

The presence of a non-base pairing base in a cfDNA may enhance the binding affinity of the cfDNA to the oxide nanowires. Thus, the cfDNA includes a non-base pairing base. The length of the non-base pairing base is preferably 3 base pairs or more, 4 base pairs or more, 5 base pairs or more, 6 base pairs or more, 7 base pairs or more, 8 base pairs or more, 9 base pairs or more, 10 base pairs or more, or equal to or less than any of the above values. In the case where the cfDNA is double-stranded, the cfDNA may be a DNA that preferably has a single-stranded base protruding from one or both of the ends of a strand (or from an end of a strand and the other end of the other strand). The length of the protrusion may be 1 base pair or more, is preferably 2 base pairs or more, and is more preferably 3 base pairs or more. The length of the protrusion may be, for example, 3 base pairs or more, 4 base pairs or more, 5 base pairs or more, 6 base pairs or more, 7 base pairs or more, 8 base pairs or more, 9 base pairs or more, 10 base pairs or more, or equal to or less than any of the above values. Alternatively, it may be converted into a single-stranded DNA or a DNA including a single-stranded DNA portion by another method, for example, but not limited to, by a heat treatment or by bringing a complementary single-stranded nucleic acid into contact with the cfDNA to partially hybridize it with the cfDNA.

The cfDNA may have a methylation-modified base but does not necessarily have a methylation-modified base. The higher the methylation level of a cfDNA is, the lower the affinity of the cfDNA for the oxide nanowires tends to be. Therefore, when cfDNAs having different methylation levels are adsorbed on oxide nanowires, cfDNAs having a lower methylation level may adsorb on the nanowires in larger amounts and may thus be concentrated to a higher degree.

Thus, in the case where the aqueous solution includes a first cfDNA having a first methylation level and a second cfDNA having a second methylation level, the first methylation level is lower than the second methylation level and the first cfDNA is concentrated to a higher degree than the second cfDNA.

(Washing Away Non-Adsorbed Component)

The non-adsorbed component may be washed away using, for example, a Tris-HCl buffer solution or water (e.g., distilled water or purified water). The non-adsorbed component is washed away under conditions suitable for washing away the non-adsorbed component. For example, the above treatment is performed under conditions that are not suitable for releasing the adsorbed DNAs from the nanowires. In other words, the treatment is not performed under conditions that are suitable for releasing the adsorbed DNAs from the nanowires.

(Liberating Adsorbed cfDNAs)

The cfDNAs adsorbed on the nanowires can be liberated from the nanowires. Liberation can be performed under conditions suitable for releasing the cfDNAs from the oxide nanowires. The cfDNAs can be released from the oxide nanowires using a solution selected from the group consisting of ethylenediaminetetraacetic acid (EDTA), a sodium chloride solution, and ethanol. Alternatively, the cfDNAs may be released from the oxide nanowires, for example, by heating. The cfDNAs may be released from the oxide nanowires under solution conditions suitable for the release and by heating. In particular, the cfDNAs can be liberated from the nanowires using a solution including a solute having a binding affinity that is 1.5 times or more, or 2 times or more, the binding affinity between the nanowires and the cfDNAs, for example, $K_A$.

(Analysis of Extracted cfDNAs)

Various DNA analysis methods can be used to analyze the liberated cfDNAs. For example, the presence of a specific DNA can be detected by performing amplification using a real-time polymerase chain reaction (RT-PCR). RT-PCR can also be used to determine the amount of a specific DNA. Thus, it is possible to measure the amount of a specific DNA included in the liberated cfDNAs. The amount of the liberated cfDNAs may be determined by digital PCR. The liberated cfDNAs may be subjected to a sequencing analysis after amplification has been performed as needed or without amplification. The liberated cfDNA may be analyzed using a DNA microarray or the like. A method in which single-stranded DNAs are amplified is also commonly known.

(Concentration of cfDNAs) In an embodiment of the present disclosure, a method for concentrating a DNA is provided. In the method for concentrating a DNA according to an embodiment of the present disclosure, first, an aqueous solution including a cfDNA having a first methylation level and a cfDNA having a second methylation level {where the first methylation level is lower than the second methylation level} is provided. In the method for concentrating a DNA according to an embodiment of the present disclosure, subsequently, oxide nanowires are brought into contact with the aqueous solution including the cfDNAs to cause the cfDNAs to adsorb on the oxide nanowires. The larger the amount of a methylation-modified bases (i.e., the higher the methylation level), the lower the binding affinity of the cfDNA to the oxide nanowires. Therefore, when the oxide nanowires and the aqueous solution are brought into contact with each other, the cfDNA having the first methylation level adsorbs on the nanowires preferentially and, as a result, the cfDNA having the first methylation level becomes concentrated. When the aqueous solution is pretreated with a Type-IV restriction enzyme, methylated DNAs are selectively cut and fragmented. Fragmentation of DNAs degrades the binding affinity of the DNAs to the nanowires. Thus, a method for concentrating DNAs according to an embodiment of the present disclosure may further include pretreating the aqueous solution with a Type-IV restriction enzyme.

The binding affinity of the nanowires to methylation-modified DNAs varies by the type of the oxide included in the oxide nanowires. Therefore, using appropriate oxide nanowires enables concentration of the cfDNA having the first methylation level.

The first methylation level is, for example, a value equal to or less than a first predetermined proportion to all the CpG sites included in the cfDNA. The first predetermined proportion may be selected from the group consisting of the following proportions: 50% or less, 45% or less, 40% or less, 35% or less, 30% or less, 25% or less, 20% or less, 15% or less, 10% or less, 5% or less, 4% or less, 3% or less, 2% or less, 1% or less, and 0%.

The second methylation level is, for example, a value equal to or less than a second predetermined proportion to all the CpG sites included in the cfDNA. The second predetermined proportion may be selected from the group consisting of the following proportions: 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, and 100%.

(Generation of Learned Model by Deep Learning and Use Thereof)

The affinity with which a methylation-modified cfDNA is bound to the nanowires varies by the material constituting the nanowires. Therefore, various cfDNAs that have been subjected to various methylation modifications may be brought into contact with nanowires composed of various materials in order to identify the binding affinities therebetween. This makes it possible to extract each cfDNA from the body fluid by the extraction method according to an embodiment of the present disclosure and to determine the type and amount of the cfDNA. In another case, machine learning is performed using the relationship between the amounts of cfDNAs on the nanowires composed of different materials, the sequences of the cfDNAs, and the methylation degrees of the cfDNAs as teaching data, and a learned model with which the sequence and/or methylation degree of a DNA, and in particular, the methylation degree of a DNA, can be determined on the basis of the amounts of cfDNAs on the nanowires composed of different materials can be established. Furthermore, cfDNAs can be extracted from each of the body fluids of a healthy person and a sick or impaired person by the extraction method according to an embodiment of the present disclosure, and the types and amounts of the cfDNAs can be determined. Machine learning is performed using the obtained data as teaching data, and a learned model with which a disease state (or disability state) can be determined on the basis of the relationship between healthy and disease states (or disability state) and the detected cfDNAs can be established. It is possible to determine whether a subject has a disease state (or disability state) by extracting cfDNAs from a body fluid sample taken from the subject by the extraction method according to an embodiment of the present disclosure, determining the types and amounts of the cfDNAs, and applying them to the learned model.

EXAMPLES

[Test Methods]

1. Preparation of DNAs

A lung cancer cell line A549, which was purchased from American Type Culture Collection (Rockville, MD, USA), was added to a RPMI-1640 medium (Wako Pure Chemical Industries, Japan) including a 5% fetal bovine serum (Thermo Fisher Scientific, MA, USA) and an antibiotic-antifungal agent (Wako Pure Chemical Industries, Japan) and maintained at 37° C. in a humidified incubator including 5% $CO_2$. Genome DNAs included in the cell line were extracted using a common phenol-chloroform method. The DNAs were fragmented to an average size of 200 bp (Covariss, MA, USA). A redistilled water including cfDNAs was prepared by the above operation. Note that, in Examples below, the redistilled water including cfDNAs was used as double-stranded DNAs (dsDNAs) unless otherwise specified.

2. Preparation of ZnO-NWs Device 2.1. Preparation of Zinc Oxide Nanowire Substrate A nanowire region was prepared by photolithography. An adhesion promotor (OAP, produced by Tokyo Ohka Kogyo Co., Ltd.) was applied to a fused silica ($SiO_2$) substrate (produced by Crystal Base Co., Ltd., Japan) having a size of 20 mm×20 mm×0.5 mm at 3000 rpm for 8 seconds. Subsequently, a positive resist (OFPR-8600LB, produced by Tokyo Ohka Kogyo Co., Ltd.) was applied at 500 rpm for 10 seconds. Then, the application was continued at 1000 rpm for 90 seconds. Subsequently, the substrate was exposed to ultraviolet radiation through a mask having a microheater pattern using a mask aligner (M-1S, produced by Mikasa Shoji Co., Ltd., Japan). After the exposure had been performed at 95° C. for 1 minute, baking was performed. After the exposure, developing was performed for 1 minute with a developing solution (NMD-3, Tokyo Ohka Kogyo Co., Ltd., Japan) to remove unexposed portions. Subsequently, rinsing was performed with distilled water. Then, drying was performed with a $N_2$ gas.

2.2. Preparation of Zinc Oxide Nanowires

On the $SiO_2$ substrate, by radio-frequency sputtering (RF sputtering) (SVC-700RF I, Sanyu Electron Co., Ltd., Japan), a ZnO thin-film layer (50 nm, 100 nm) was formed. Subsequently, ZnO-NWs were synthesized by hydrothermal synthesis. ZnO-NWs growth solutions having various concentrations were prepared using zinc nitrate and hexamethylene tetramine (Alfa Aesar, A Joshnoson Mathey Company, USA), that is, 10 to 100 mM, at 95° C. over 3 hours. Finally, the photoresist was removed with acetone.

2.3. Preparation of Patterned Microchannel with Flat Surface

A silicon wafer (Advantech Co., Ltd., United Kingdom) was spin-coated with a negative photoresist SU-8 (SU-8 3050, Nippon Kayaku Co., Ltd., Japan) using a spin coater (IF-D7, Mikasa Shoji Co., Ltd., Japan) at 500 rpm for 5 seconds and subsequently at 1000 rpm for 30 seconds. The coated silicon wafer was soft-baked at 95° C. for 45 minutes. Finally, unexposed portions were removed with a SU-8 developing solution for 5 minutes and subsequently with isopropanol alcohol (Wako Pure Chemical Industries, Ltd., Japan).

2.4. Preparation of Patterned Microchannel Chaotic Mixer

A silicon wafer (Advantech Co., Ltd., United Kingdom) was spin-coated with a negative photoresist SU-8 (SU-8 3050, Nippon Kayaku Co., Ltd., Japan) using a spin coater (IF-D7, Mikasa Shoji Co., Ltd., Japan) at 500 rpm for 10 seconds and subsequently at 5000 rpm for 30 seconds. The coated silicon wafer was soft-baked at 95° C. for 15 minutes. The wafer was irradiated with ultraviolet (UV) light through a microchannel pattern mask with a mask aligner (M-1S, Mikasa Shoji Co., Ltd., Japan). Subsequently, the microchannel substrate was heated at 65° C. for 1 minute and at 95° C. for 3 minutes. Then, the above operation was repeated. That is, SU-8 (SU-8 3005, produced by Nippon Kayaku Co., Ltd.) was rotated at 500 rpm for 10 seconds and at 2000 rpm for 30 seconds to form a chaotic mixer structure. Subsequently, soft baking was performed at 95° C. for 2.30 minutes. Then, the wafer was irradiated with ultraviolet (UV) light through a microchannel pattern mask with a mask aligner (M-1S, Mikasa Shoji Co., Ltd., Japan). Subsequently, the microchannel substrate was heated at 65° C. for 1 minute and at 95° C. for 1.30 minutes. Finally, unexposed portions were removed with a SU-8 developing solution for 10 minutes and subsequently with isopropanol alcohol (produced by Wako Pure Chemical Industries, Ltd., Japan).

2.5. Preparation for Substrate Joint

Using a soft plasma etching device (SEDE-PFA, Meiwafosis Co., Ltd., Japan), the PDMS microchannel was bonded to the ZnO-NWs substrate and, subsequently, a small amount of PDMS mixture was poured into the gap between the substrate and the PDMS. The device prepared above was heated at 80° C. for 1 hour and then cooled to room temperature. Subsequently, introduction and discharge holes were formed in the PDMS using a 0.5-mm UNI CORE (Harris, USA). A PEEK tube (ICT-55P, Institute of Microchemical Technology Co., Japan) was inserted directly into each of the above holes.

3. Evaluation of Properties of Zinc Oxide Nanowires (ZnO-NWs)

3.1. Scanning Electron Microscope (SEM) Imaging

The morphologic characterization of the nanowires was conducted using a scanning electron microscope (Supra 40VP, Carl Zeiss, Germany) operated at an acceleration voltage of 20 kV. The range of the sizes of the nanowires was measured using software ImageJ.

4. Characteristic Evaluations of Interaction Between Zinc Oxide Nanowires (ZnO-NWs) and DNAs 4.1. Fourier Transform Infrared Spectroscopy (FTIR) Analysis FTIR was conducted to study the interaction between zinc oxide nanowires and a nucleic acid base or a DNA. An FT-IR spectroscopy test was conducted using a Nicolet™ iS50 FTIR Spectrometer (Thermo Fisher Scientific, MA, USA) at wavenumbers of 400 to 650 cm-1. All spectra were recorded with 1000 scans at minimum.

5. Incorporation of DNAs with Zinc Oxide Nanowires (ZnO-NWs)

5.1. Introduction of DNAs to Nanowire Device

Into the device, 50 μl of redistilled water containing 1 ng/μl of a DNA sample (200 bp) was introduced with a syringe pump at a flow rate of 1 μl/min and then collected in order to determine capture efficiency. This sample is referred to as "collected DNA sample". Subsequently, distilled water was introduced into the device to wash away uncaptured DNAs on the ZnO-NWs.

5.2. Quantitative Real-Time Polymerase Chain Reaction (qRT-PCR) Analysis

The efficiency with which DNAs were captured on the ZnO-NWs was determined by calculating the difference in concentration between the introduced and collected DNA samples by qRT-PCR. The reaction mixture included 2 μl of DNA, 5 μl of TaqMan Gene Expression Master Mix (5'-CTGTTCGACAGTCAGC-3': SEQ ID NO: 16) (Thermo Fisher Scientific, MA, USA), 2.75 μl of distilled water, and 0.25 μl of Primer GAPDH Housekeeping Gene (forward: 5'-CCTCCCGCTTCGCTCTCT-3': SEQ ID NO: 17 and reverse: 5'-GGCGACGCAAAAGAAGATG-3': SEQ ID NO: 18). All of the reactions were conducted by performing an initial modification step at 95° C. for 10 minutes, 40 cycles at 95° C. for 10 seconds, and annealing at an annealing temperature of 55° C. for 1 minute. The qRT-PCR was conducted in a 96-well plate on PikoReal 96 Real-Time PCR System (Thermo Fisher Scientific, MA, USA).

6. Preparation of Metal Nanowires 6.1. Preparation of ZnO Nanowires

A cleaned quartz substrate (produced by Crystal Base Co., Ltd.) having a size of 20 mm size of 20 mm×20 mm×0.5 mm was spin-coated with 1,1,1,3,3,3-hexamethyldisilazane (OAP, Produced by Tokyo Ohka Kogyo Co., Ltd.) and OFPR-8600 (produced by Tokyo Ohka Kogyo Co., Ltd.). A microchannel pattern having a length of 10 mm and a width of 5 mm was subsequently formed by photolithography. Then, the above substrate was immersed in an NMD-3 solution (produced by Tokyo Ohka Kogyo Co., Ltd.) to develop a pattern used as a region in which nanowires were to be grown. On the pattern, a ZnO seed layer was formed by performing sputtering for 10 minutes using an RF sputtering device (produced by Sanyu Electron Co., Ltd., SC-701Mk ADVANCE). Using a hydrothermal method, the substrate was immersed in a liquid mixture including 40-mM hexamethylenetetramine (HMTA, Wako Pure Chemical Industries, Ltd.) and 40-mM zinc nitrate hexahydrate (Thermo Fisher Scientific K. K.) and then heating was performed at 95° C. for 3 hours to cause nanowires to grow. The grown nanowires were nanowires having a thickness of about 100 nm and a length of about 2 μm.

6.2. Atomic Layer Deposition (ALD) of $Al_2O_3$, $TiO_2$, and $SiO_2$ Layers

After the preparation of the ZnO nanowires, atomic layer deposition (ALD) was performed using an ALD device (Savannah G2, Ultratech) in order to form metal oxide thin-layers having a thickness of about 5 to 10 nm. The conditions used vary by the type of the metal oxide: i) $Al_2O_3$ (precursor: trimethylaluminum (TMA) and ozone, temperature: 150° C., 55 cycles), ii) $TiO_2$ (precursor: tetrakis(dimethylamide)titanium (TDMAT) and water, temperature: 150° C., 125 cycles), iii) $SiO_2$ (precursor: tris(dimethylamino)silane (TDMAS) and ozone, temperature: 150° C., 55 cycles)

6.3. Incorporation of Nanowires into Microchip

A polydimethylsiloxane (PDMS) mold (length: 10 mm, width: 5 mm, depth: 10 μm, inlet and outlet holes: 0.5 mm) was prepared using Silpot184 (produced by Dow Toray Co., Ltd.) and Catalyst Silpot184 (produced by Dow Toray Co., Ltd.) at a ratio of 10:1. The surfaces of the PDMS mold and the nanowire substrate were treated with a plasma etching device (produced by Meiwafosis Co., Ltd.). Subsequently, the two substrates were bonded to each other and then heated at 180° C. for 2 minutes. Then, a 0.5-mm PEEK tube (Institute of Microchemical Technology Co., Ltd.) was inserted into both holes: inlet and outlet.

6.4. Evaluation of Properties of Nanowires Using FESEM and STEM-EDS

The state of the surfaces of the ZnO nanowires grown by the hydrothermal method was observed with a field emission electron scanning microscope (FESEM) (SUPRA 40VP, Carl Zeiss AG, Germany). Element mapping of the ZnO-coated nanowires was performed using a scanning transmission electron microscope (STEM-EDS) having an energy dispersive x-ray spectroscopy (STEM-EDS) function operated at an acceleration voltage of 30 kV. Images were formed at 512×384 pixels and a scanning rate of 0.1 ms. The images were integrated 100 cycles. Images were formed using peaks corresponding to Zn Kα (8.630 keV), O Kα (0.525 keV), Al Kα (1.486 keV), Ti Kα (4.508 keV), and Si Kα (1.739 keV).

7. Measurement of Zeta Potential

The zeta potential of DNAs in 50 ng/μL of a Millipore aqueous solution was measured at 25° C. with a dynamic light scattering spectrophotometer (ZETASIZER Nano-ZS Malvern Instruments Limited Japan, Hyogo, Japan). As for the metal oxide nanowires, $ZnO/Al_2O_3$ NWs, $ZnO/TiO_2$ NWs, and $ZnO/SiO_2$ NWs were prepared on a 2.6 cm×3.7 cm glass substrate, and the zeta potentials of the nanowires were measured in an aqueous solution at a temperature of 25° C. using ELSZ-2000 (Otsuka Electronics Co., Ltd., Hirakata City, Japan).

8. Capture of DNAs Using Nanowire Microfluid Device

The DNAs, primers, and probe used in this test were purchased from Invitrogen and Themo Fischer Scientific. Table 1 lists the sequences. Stock DNAs were dissolved in Millipore water to prepare a 50 ng/μL DNA. The pH of the DNA solution was changed to 3, 5, 7, or 10 using hydrochloric acid (HCl, produced by FUJIFILM Wako Pure Chemical Corporation) and a solution of sodium hydroxide (NaOH, produced by Wako Pure Chemical Industries, Ltd.). The pH was measured with a pH meter (produced by HORIBA Scientific Co., Ltd.). The DNA capture test was conducted using a syringe pump system (KDS-200, produced by KD Scientific) at a flow rate of 5 μL/min. In order to remove possible contaminants, 50 μL of Millipore water was introduced. Subsequently, 50 μL of 50 ng/L DNA was introduced to the inlet of the microfluidic device. The collected amount was charged into a 1-mL centrifuge tube.

TABLE 1

DNA sequences used (corresponding to sequence numbers 1-15, respectively)

| Oligonucleotides | Sequence (5'-3') |
|---|---|
| Probe | FAM-ATCGCGCTCTCGCGCTGACGG |
| Forward primer | ACGCGTACTGCGGTCG |
| Reverse primer | GCGTACGCGCGACG |
| 0% methylation/ 61 bases | ATACGCGTACTGCGGTCGCGATCGCGCTCTCGCGCTGACGGTGCGTCGCGCGTACGCGATT |
| 5% methylation | ATACmGCGTACTGCGGTCGCGATCGCGCTCTCGCGCTGACGGTGCGTCGCGCGTACGCGATT |
| 10% methylation | ATACmGCGTACTGCGGTCGCGATCGCGCTCTCGCGCTGACGGTGCGTCGCGCGTACGCmGATT |
| 20% methylation | ATACmGCGTACTGCGGTCGCGATmGCGCTCTCGCGCTGACGGTGCmGTCGCGCGTACGCmGATT |
| 40% methylation | ATACmGCGTACTGCmGGTCmGCGATCmGCGCTCTCGCmGCTGACGGTGCmGTCGCGCmGTACGCmGATT |
| 80% methylation | ATACmGCmGTACTGCmGGTCmGCmGATCmGCmGCTCTCmGCmGCTGACmGGTGCmGTCmGCmGCmGTACmGCmGATT |
| 80 bases | ATACmGCGTACTGCGGTCGCGATmGCGCTCTCGCGCTGACGGTGATGGACTTGACTAAGGTTGCmGTCGCGCGTACGCmGATT |
| 100 bases | ATACmGCGTACTGCGGTCGCGATCmGCGCTCTCGCGCTGACGGTGATGGACTTGACTAAGGTAGGTTATGACAGGCTTAGAATGCmGTCGCGCGTACGCmGATT |
| 2D | ATACmGCGTACTGCGGTCGCGATCGCGCTCTCGCGCTGACGGTGCGTCGCGCGTACGCmGATT |
| 2C | ATACmGCmGTACTGCGGTCGCGATCGCGCTCTCGCGCTGACGGTGCGTCGCGCGTACGCGATT |
| 4D | ATACmGCGTACTGCGGTCGCGATCmGCGCTCTCGCGCTGACGGTGCGTCGCGCGTACmGCmGATT |
| 4C | ATACmGCmGTACTGCGGTCGCGATCGCGCTCTCGCGCTGACGGTGCGTCGCGCGTACmGCmGATT |

9. Quantification of DNAs

The amount of DNAs collected was analyzed using a PIKOREAL 96 real-time polymerase chain reaction (RT-PCR) system (Thermo Fischer Scientific Inc). A mixture including 1 μL of the DNA solution, 3.5 μL of Millipore water, 5 μL of TaqMan$^{(R)}$ Gene Expression Master Mix (Applied Biosystems, Thermo Fischer Scientific Inc.), and 0.5 μL of Custom TaqMan$^{(R)}$ Gene Expression Assays (Applied Biosystems, Thermo Fischer Scientific Inc.) was pipetted on a 96-well reaction plate. Then, sealing was performed with an optical seal (Applied Biosystems, Thermo Fischer Scientific). Subsequently, RT-PCR was conducted. Table 1 lists details of sequences of the primers and the probe. As for the RT-PCR protocol, a cycle condition in which a cycle of 50° C. for 2 minutes, 95° C. for 10 minutes, 95° C. for 15 seconds, and 60° C. for 1 minute was repeated 50 times was employed.

(Computational Expression for Capture Efficiency)

$$\text{Capture efficiency (\%)} = (\text{Amount of DNAs introduced} - \text{Amount of DNAs discharged}) / \text{Amount of DNAs introduced} \times 100\%$$

Example 1: Binding of cfDNAs to Nanowires

Figure 1B:
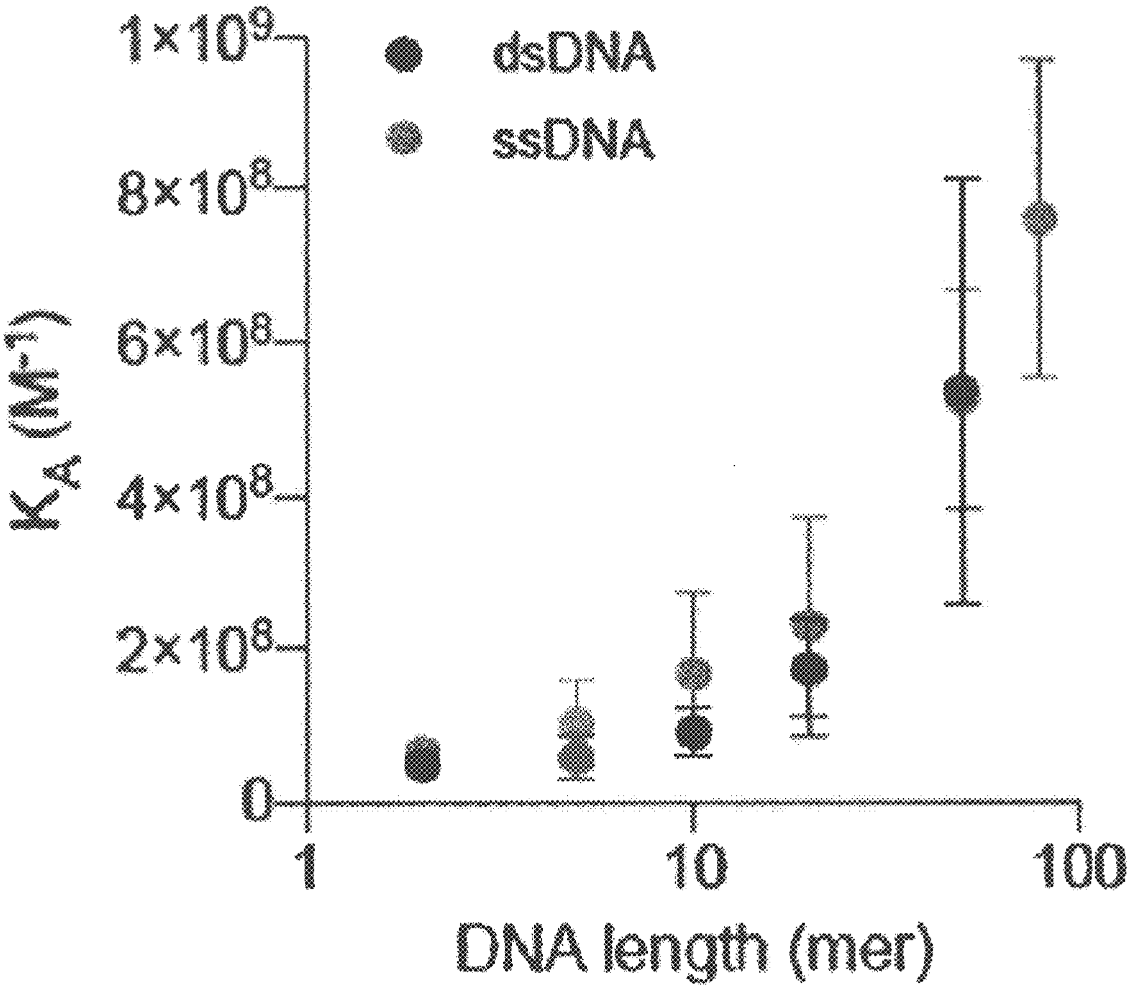
FIG. 1B illustrates the relationship between the length of cfDNAs brought into contact with nanowires and binding affinity (KA) to the nanowires.

ZnO nanowires disposed in a microfluidic device were prepared. Whether cfDNAs were captured by the nanowires was determined. Various redistilled water solutions containing double-stranded cfDNAs (molecule average: 200 bp) at different concentrations (0.01 to 50 ng/μl) were prepared. The solutions were brought into contact with the zinc oxide nanowires, and the amounts of DNAs captured were measured. FIG. 1-1 is a semilogarithmic graph illustrating the results. As illustrated in FIG. 1-1, as for the cfDNAs, it was confirmed that there was the correspondence between DNA concentration and captured DNA which can be approximated with a sigmoid curve. That is, it was suggested that the interaction between the cfDNAs and the nanowires was a phenomenon that may form an equilibrium state.

Figure 2:
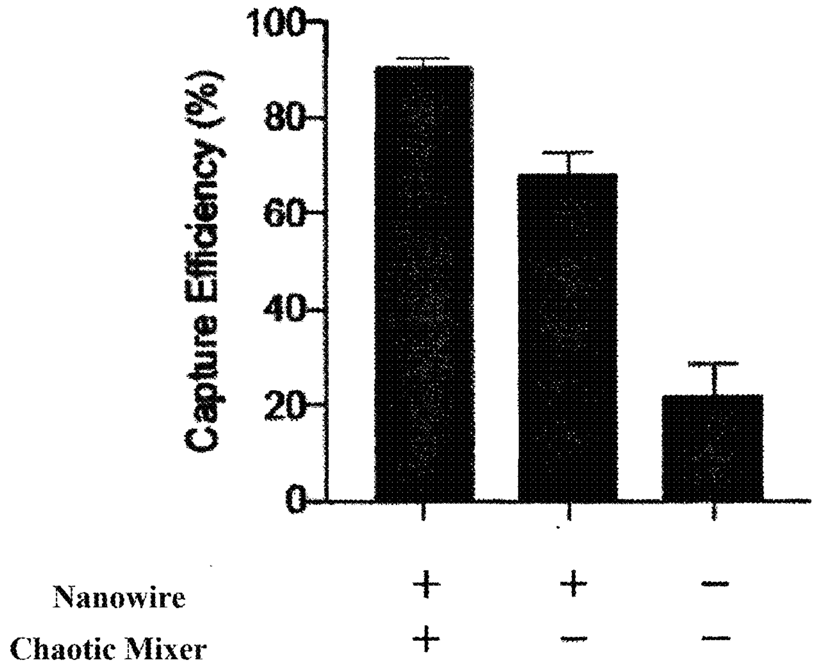
FIG. 2 illustrates the impacts of the presence of nanowires and the presence of a chaotic mixer on the efficiency with which cfDNAs are captured.
Figure 3:
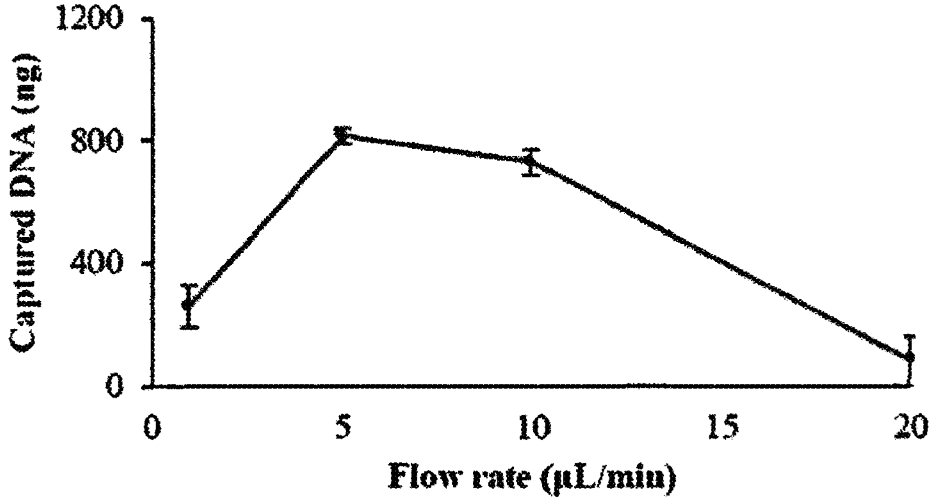
FIG. 3 illustrates the relationship between the amount of DNAs captured by the device prepared in Examples and the flow rate at which cfDNAs are introduced to the device.

Next, the relationship between the length of DNAs and the interaction between the DNAs and the nanowires was determined. FIG. 1-2 illustrates the results. As illustrated in FIG. 1-2, both double-stranded DNAs (dsDNAs) and single-stranded DNAs (ssDNAs) had strong affinity for the nanowires. The longer the DNAs were, the higher the affinity was. In a region in which the DNA length is small (e.g., 20 base pairs or less), the single-stranded DNAs had stronger affinity for the nanowires than the double-stranded DNAs.

Furthermore, a thermodynamic analysis of binding of the single-stranded DNAs (ssDNAs) and the double-stranded DNAs (dsDNAs) to zinc oxide nanowires was conducted. Table 2 lists the results.

TABLE 2

Thermodynamic constants for cfDNA of various lengths

| | ΔG (kcal mol$^{-1}$) | ΔH (kcal mol$^{-1}$) | −TΔS (kcal mol$^{-1}$) |
|---|---|---|---|
| SSDNA | | | |
| 2 mer | −10.63 | −100.67 | 90.23 |
| 5 mer | −10.87 | −74.97 | 64.13 |
| 10 mer | −11.00 | −104.70 | 93.47 |
| 20 mer | −11.27 | −88.10 | 84.23 |
| 50 mer | −11.47 | −80.90 | 69.43 |
| 80 mer | −11.93 | −105.67 | 93.87 |
| dsDNA | | | |
| 2 bp | −10.67 | −103.37 | 92.67 |
| 5 bp | −10.57 | −118.00 | 107.27 |
| 10 bp | −10.83 | −101.60 | 90.57 |
| 20 bp | −11.23 | −457.00 | 445.67 |
| 50 bp | −11.73 | −511.00 | 499.33 |
| 80 bp | −12.27 | −812.33 | 800.33 |

As is clear from Table 2, the binding between the cfDNAs and the nanowires is an exothermic reaction that occurs spontaneously at room temperature.

In addition, the efficiencies with which cfDNAs (molecule average: 200 bp) were captured in the case where the chaotic mixer formed in the channel was present or absent and in the case where the nanowires were absent, that is, glass surface, were compared with one another. FIG. 2 illustrates the results. As illustrated in FIG. 2, the adsorption efficiency was increased in the case where the nanowires were present, compared with the adsorption of the cfDNAs onto the glass surface. Moreover, the adsorption of the cfDNAs on the nanowires was enhanced in the case where the chaotic mixer was present, compared with the case where the chaotic mixer was absent. This suggests that, although the presence of the chaotic mixer in the channel is not essential, the presence of the chaotic mixer enabled the cfDNAs to be stirred in the channel and increased the likelihood of the cfDNAs coming into contact with the nanowires and this enhanced the adsorption of the cfDNAs to the nanowires.

Next, the relationship between the flow rate of the cfDNA solution and the efficiency with which cfDNAs (molecule average: 200 bp) were captured was determined. When the study was conducted while the flow rate was changed within a range of 1 to 20 μl/min, as for the above nanowire region, the efficiency with which cfDNAs were captured on the nanowires was the highest when the flow rate was 5 to 10 μl/min. This suggests that, for increasing the flow rate, it may be advantageous to widen the nanowire region.

An attempt was made to isolate cfDNAs from a urine sample with a commercial kit. The cfDNA extraction was performed in accordance with the recommended protocol. A reagent QIAamp Circulating Nucleic Acid Kit (Qiagen, Germany) was used for isolating cfDNAs from 1 ml of urine. A lysate buffer (ACL) containing 1 μg of carrier RNAs was prepared prior to the test. To a 50-mL tube, 125 μL of a proteinase K solution, 1 mL of an ACL buffer solution, 250 μL of an ATL buffer solution, and 1 mL of urine were added in order. The resulting mixture was uniformly stirred with a vortex mixer for 30 seconds and then incubated at 60° C. for 30 minutes. After stirring had been performed with a vortex mixer for 30 seconds, 3.6 mL of ACB was added. Then, stirring was performed with a vortex mixer for 30 seconds to form a homogeneous mixture. The final mixture was incubated on ice for 5 minutes. A spin column equipped with an extender was attached to a manifold QIAvac 24 Plus (Qiagen, Germany) connected to a vacuum pump. The final mixture was added to the spin column. The vacuum pump was driven until the final mixture had been completely drawn through a silica membrane. Subsequently, 600 μL of a cleaning buffer solution 1 (ACW1), 750 μL of a cleaning buffer solution 2 (ACW2), and 750 μL of a cleaning buffer solution 3 (100% ethanol) were sequentially added to the spin column arranged to pass through a silica membrane. In a drying step, the spin column placed in a 2-mL collection tube was centrifuged at 14,000 rpm for 3 minutes and, subsequently, the spin column was charged into a 1.5-mL elution tube. Finally, 50 μL of an elution buffer was carefully applied to the center of the spin column, and centrifugation was performed for 1 minute at 14,000 rpm. The recovery ratio of DNAs was about 5% regardless of DNA concentration (0.1 to 1 ng/μL).

cfDNAs were extracted from urine samples (1 ml) of various cancer patients. As for the patients, urine samples of patients with glioma (stage 2), anaplastic astrocytoma (stage 3), oligodendroglioma (stage 2), glioblastoma (stage 4), diffuse astrocytoma (stage 4), and glioblastoma (stage 4) were taken. As described above, an attempt was made to extract cfDNAs from the above samples with a microfluidic device including zinc oxide nanowires according to an embodiment of the present disclosure and with a commercial kit. The urine samples were cryopreserved until just before extraction. The urine samples were thawed immediately before extraction and used within 3 hours after thawing. The thawed urine samples were centrifuged at 3,000×g for 15 minutes to remove the precipitate, and the supernatant was used as a sample. Table 3 lists the results.

TABLE 3

Extraction of cfDNAs from urine samples

| | samples | nanowires (ng/mL) | commercial kit (ng/mL) |
|---|---|---|---|
| 1 | glioma (stage 2) | 98.09 | undetectable |
| 2 | anaplastic astrocytoma (stage 3) | 68.94 | undetectable |
| 3 | oligodendroglioma (stage 2) | 21.61 | undetectable |
| 4 | glioblastoma (stage 4) | 87.16 | undetectable |
| 5 | diffuse astrocytoma (stage 4) | 19.56 | undetectable |
| 6 | glioblastoma (stage 4) | 8.41 | undetectable |

As listed in Table 3, it was not possible to extract a certain amount of cfDNAs which was equal to or more than the detection limit from the urine samples with the commercial kit. In contrast, large amounts of cfDNAs could be extracted by the method according to an embodiment of the present disclosure, in which cfDNAs were adsorbed on oxide nanowires.

Example 2: Type of Oxide Nanowires and Capture of cfDNAs

Various types of nanowires including zinc oxide (ZnO) nanowires as cores and oxides that completely covered the peripheries of the cores were prepared. The structures of the nanowires were inspected by element mapping. FIG. 4 illustrates the results. As illustrated in FIG. 4, it was confirmed that each of silicon dioxide ($SiO_2$), aluminum oxide ($Al_2O_3$), and titanium dioxide ($TiO_2$) completely covered the zinc oxide nanowires.

cfDNAs (molecule average: 200 bp) were applied to a microfluidic device including the above coated nanowires buried therein in order to measure capture efficiency. FIG. 5 illustrates the results. The upper right-hand panel of FIG. 5 illustrates the zeta potentials of the various types of coated nanowires. The ZnO nanowires and the aluminum oxide-coated nanowires had a positive zeta potential, while the silicon oxide-coated nanowires and the titanium oxide-coated nanowires had a negative zeta potential. DNAs had a negative zeta potential. In spite of this, the efficiencies with which cfDNAs were captured on the various types of coated nanowires were all about 80%. It was understood that the zeta potential of the nanowire surface does not greatly affect capturing of cfDNAs on the nanowires. Note that, when nanowires covered with nickel oxide (NiO) were prepared and the same test as described above was conducted, the cfDNA capture efficiency of the nanowires was about 70%.

The impacts of the pH of the solution on the efficiency with which the cfDNAs (molecule average: 200 bp) were captured on the nanowires were determined. The aluminum oxide-coated nanowires had the highest capture efficiency at a pH of 5 to 7, while the other types of nanowires had the highest capture efficiency at a pH of 7.

Figure 6A:
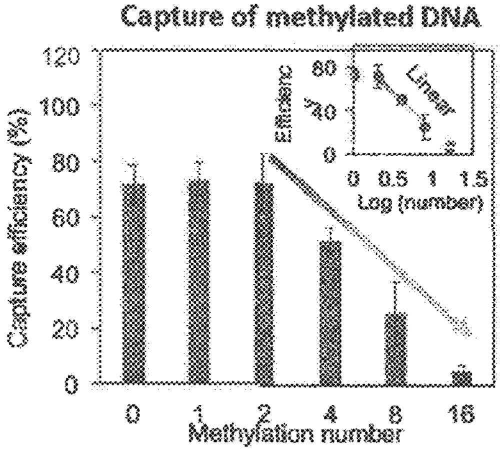
FIG. 6A-C illustrates the efficiencies with which cfDNAs having a methylation-modified base are captured on the nanowires.
Figure 6B:
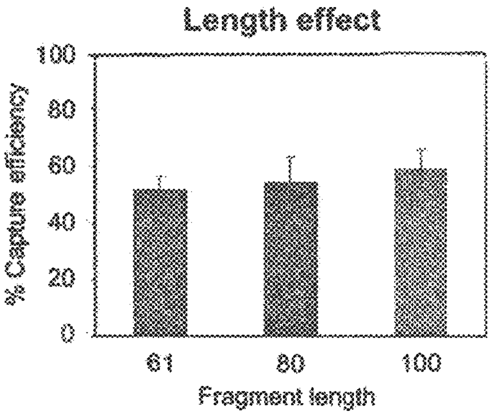
Figure 6C:
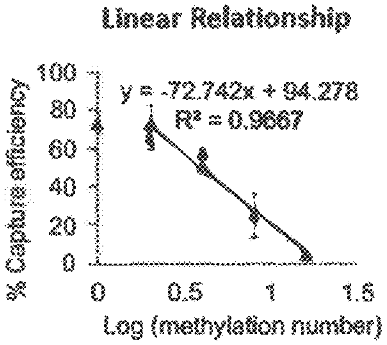

The impacts of DNA methylation on the efficiency with which the cfDNAs were captured on the nanowires were determined. The methylated DNAs used were the cfDNAs (5% to 80% methylated cfDNAs) listed in Table 1. The relationship between methylation level and cfDNA capture efficiency was represented by a graph, with the horizontal axis representing the number of methylated bases and the vertical axis representing the efficiency with which the cfDNAs were captured on the nanowires. The upper left-hand portion of FIG. 6 illustrates the results. As illustrated in the upper left-hand panel of FIG. 6, the capability of cfDNAs to bind to the nanowires became degraded when the cfDNAs had more than two methylated bases. The nanowires were capable of detecting the methylation of DNAs with high sensitivity. Another test was conducted using cfDNAs having four methylation bases and various lengths. As illustrated in the upper right-hand panel of FIG. 6, the longer the DNAs were, the higher the capture efficiency was.

Figure 7:
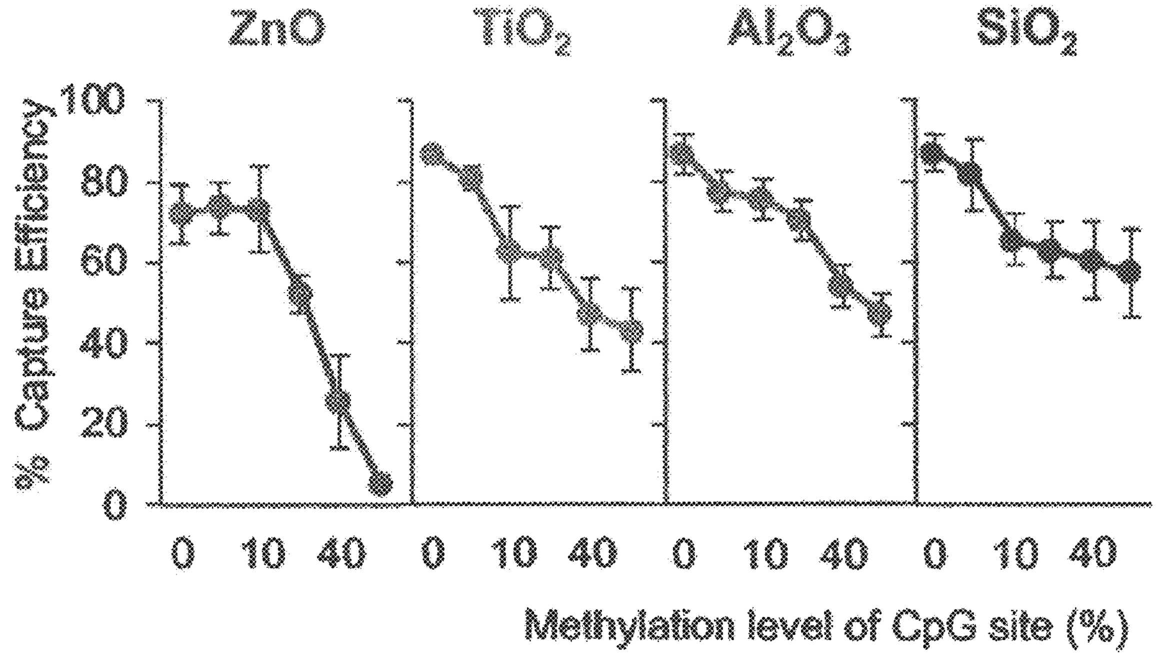
FIG. 7 illustrates the impacts of methylation level on the efficiencies with which cfDNAs are captured on the various oxide nanowires.

The efficiency of capture of cfDNAs including methylated bases (see Table 1) was determined using the various types of nanowires covered with different oxides. As illustrated in FIG. 7, the higher the proportion of methylation of the CpG sites, the lower the DNA capture efficiency regardless of the types of the oxide covering the nanowires. However, the degree by which the capture efficiency was reduced varied by the type of the oxide (FIG. 7).

Figure 8:
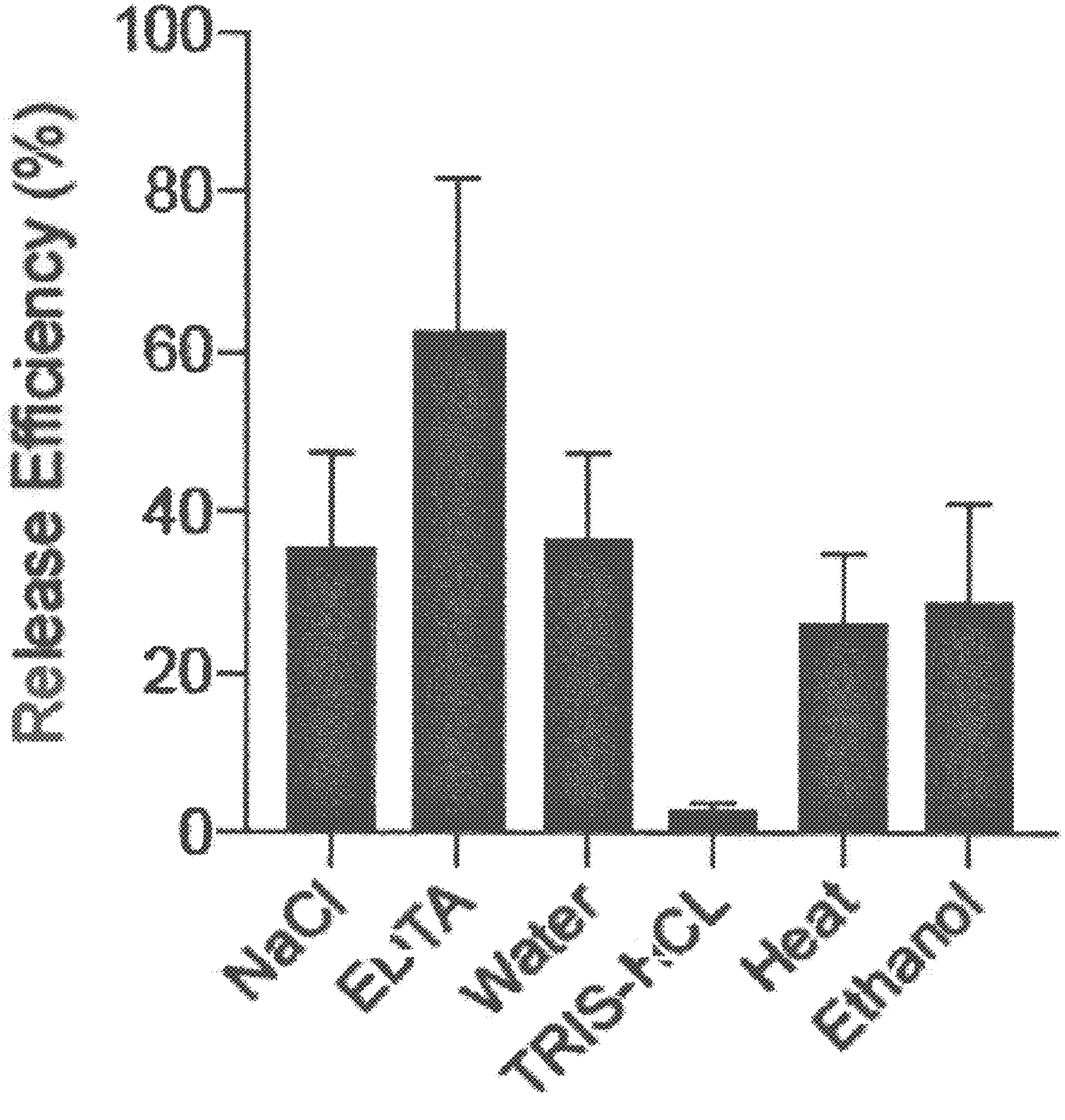
FIG. 8 illustrates the impacts of various eluting solutions on the efficiency with which cfDNAs are eluted from nanowires.

The factor that facilitates the release (elution) of cfDNAs from the nanowires was searched. The eluting solutions used were a NaCl solution (0.1 M), an EDTA solution (composition: 10 μM EDTA), water, a Tris-HCl solution (0.1 M), heat (60° C.), and a 10% aqueous ethanol solution. Into a microfluidic device, 50 μl of a specific one of the above eluting solutions was injected at a flow rate of 5 μl/min to elute the cfDNAs (average: 200 bp) bound to the nanowires. FIG. 8 illustrates the results. As illustrated in FIG. 8, the Tris-HCl solution hardly eluted the DNAs from the nanowires. In contrast, the other eluting solutions all had an elution efficiency of more than 30 percent. The EDTA solution had a cfDNA elution efficiency of about 60%.

Example 3: FT-IR Analysis

Figure 9:
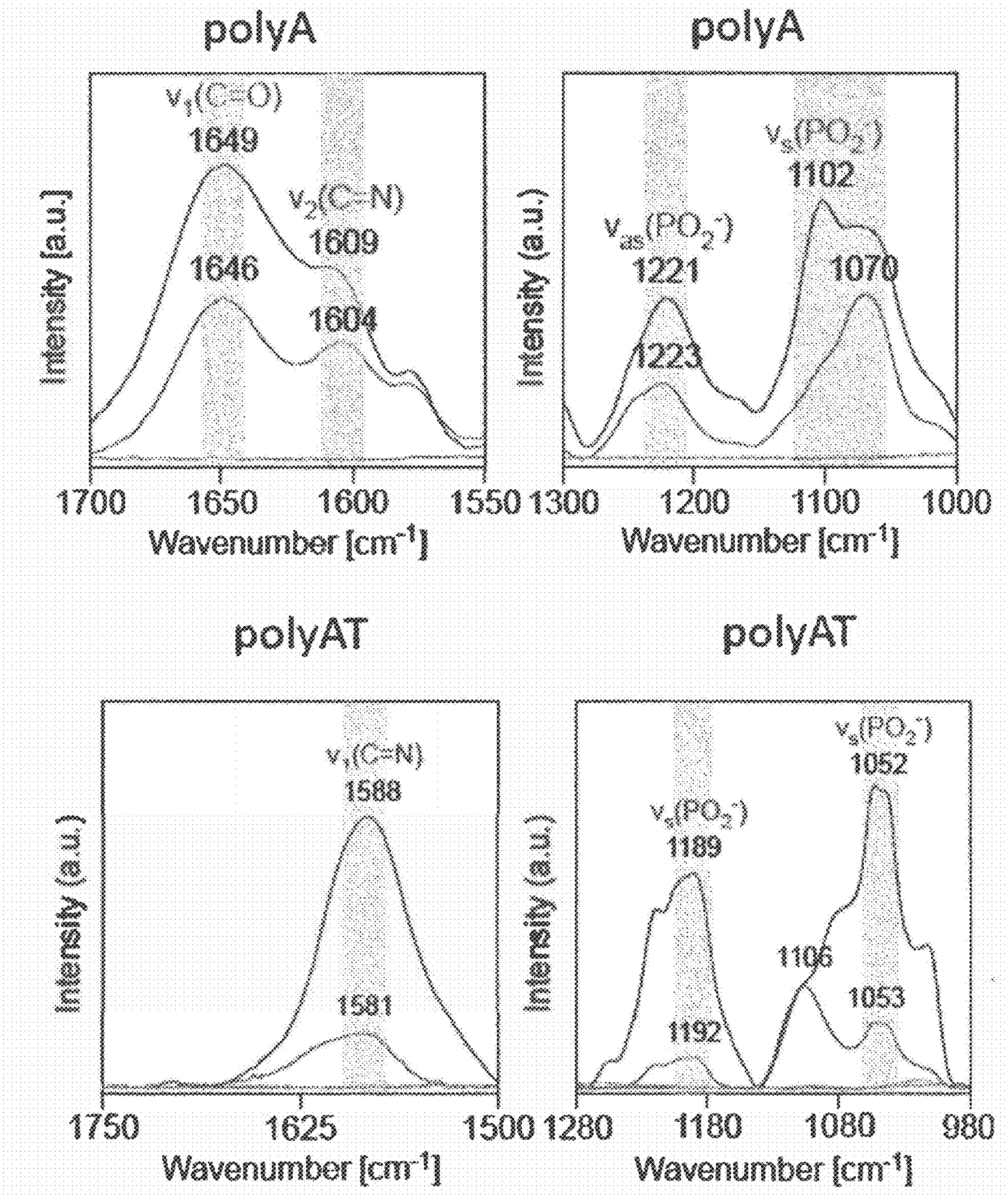
FIG. 9 illustrates the results of IR spectrum analyses conducted before and after single-stranded cfDNAs (upper panels) and double-stranded cfDNAs (lower panels) are brought into contact with nanowires.

The interaction between cfDNAs and the nanowires was analyzed using FT-IR spectrometry. On the basis of the phenomenon in which the IR spectrum becomes reduced when cfDNAs are bound to the nanowires, the part of DNAs which is responsible for the interaction with the nanowires was clarified. FIG. 9 illustrates the results. As illustrated in FIG. 9, parts of the spectrum which corresponded to V1 (C═O) and V2 (C═N) were reduced as a result of the interaction with the nanowires. This clarified that both base portions and phosphate backbone portions of DNAs interact with the nanowires.

Example 4: Molecular Dynamics Simulation

A molecular dynamics simulation (MD simulation) of the interaction between the oxide nanowires and cfDNAs was conducted.

The molecular force field model used was basically the CHARMM36 force field. The model of ZnO nanowires was employed from a thesis (G. Nawrocki, M. Cieplak, Phys. Chem. Chem. Phys., 2013, 15, 13628). ZnO was prepared so as to have a hexagonal Wurtzite-type structure having lattice constants a=0.325 nm and c=0.52 nm and such that the (1 0 1 1)-plane was oriented in the direction perpendicular to the surface (z-axis direction). When the unit lattice was enlarged 10, 16, and 2 times in the x, y, and z-axis directions, respectively, the cell sizes in the direction parallel to the surface were Lx=Ly=5.2 nm. After force calculation, the ZnO particles were assumed as an absolutely fixed substrate by setting the velocity to zero in velocity renewal. Periodic boundary conditions were set only in the x and y directions. In order to an aqueous solution including DNAs and the like on the surface of ZnO and calculate an aqueous solution system in the vicinity of the substrate, a wall potential was placed at the positions of z=0 and z=Lz (using the setting of gromacs, Wall) in order to prevent evaporation of the aqueous solution. The Wall is constituted by particles having the same interaction parameters as graphite carbon and LJ9-3 interacts with particles that go beyond the wall. The density of particles in the wall was set to 38.6/nm$^3$. As for details of the molecular dynamics calculation, the time step was set to 2 fs. As for interatomic interaction, the Lennard-Jones interaction was cut off to 1.2 nm using switching function. Electrostatic interaction was calculated using a two-dimensional Particle mesh Ewald method. For controlling temperature, velocity rescaling was used. The temperature was maintained at 300 K.

Figure 10:
FIG. 10 illustrates the results of molecular dynamics (MD) simulations of 5-mer single-stranded DNAs on the surfaces of nanowires.

The results of the MD simulation show that the amounts of time during which the 1-mer and 2-mer single-stranded DNAs interacted with the oxide nanowires were small and, even when the DNAs were bound to the oxide nanowires, they became detached immediately. In contrast, single-stranded DNAs having a length of 3 mer or more were adsorbed on the surfaces of the oxide nanowires in a relatively stable manner. The results of the MD simulation of the 5-mer single-stranded DNAs confirmed that, primarily, the base portions of the single-stranded DNAs interacted with the nanowires. FIG. 10 illustrates a representative example of the interaction. It was confirmed that, as illustrated in FIG. 10, the bases interacted with the oxide nanowires with a water molecule layer interposed therebetween. It was clarified that, in 3-mer and 5-mer single-stranded DNAs, the bases are responsible for the interaction with the oxide nanowires, polyvalent effects are produced as a result of the interaction of a plurality of bases with the oxide nanowires, and this stabilizes the adsorption of DNAs on the oxide nanowires. On the other hand, when dsDNAs do not have a non-base pairing base, such short dsDNAs were not capable of interacting with the oxide nanowires in a stable manner.

Figure 11:
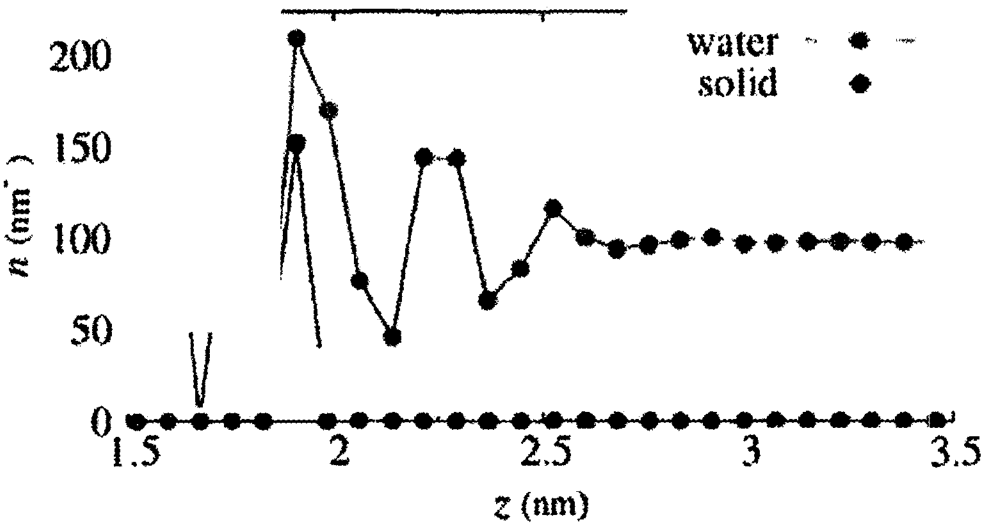
FIG. 11 illustrates the relationship between the positions at which nanowires and water molecules are present, which are calculated by MD simulations.
Figure 12:
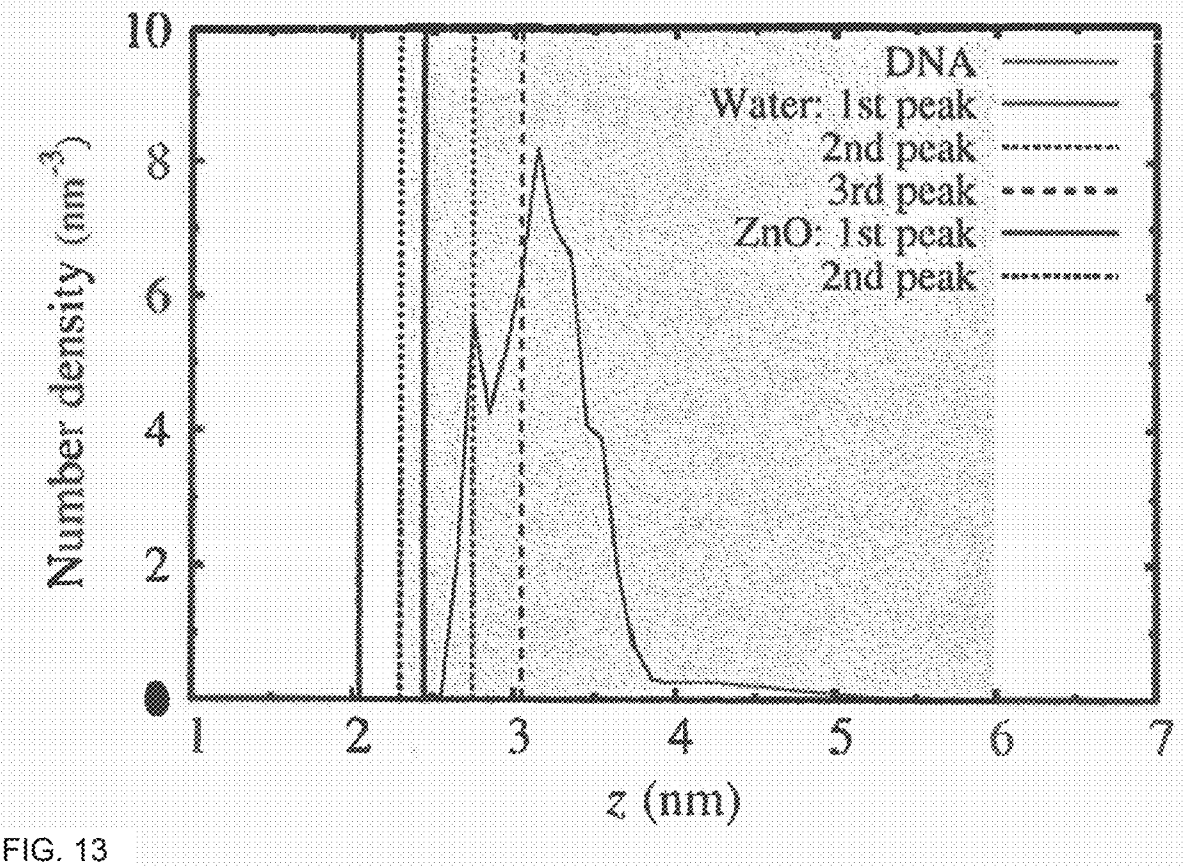
FIG. 12 illustrates the relationship between the positions at which nanowires, water molecules, and single-stranded DNAs are present, which are calculated by MD simulations.
Figure 13:
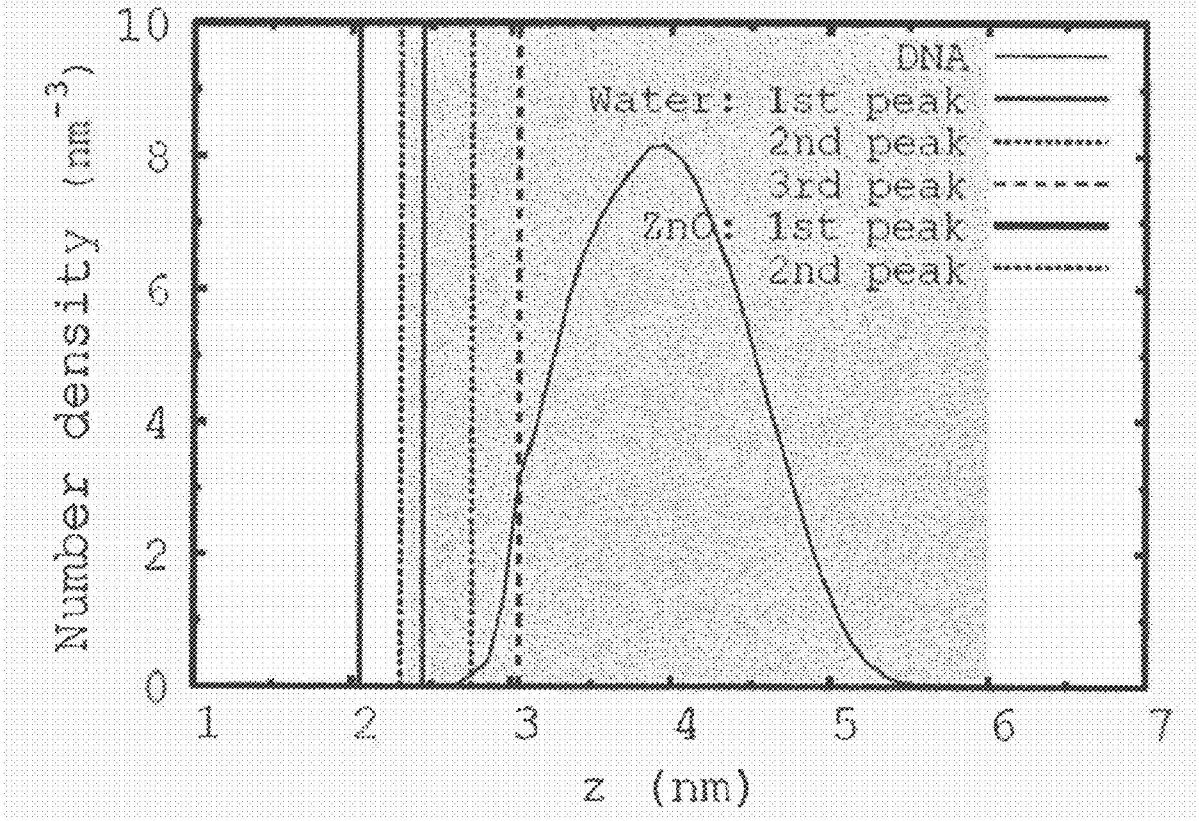
FIG. 13 illustrates the relationship between the positions at which nanowires, water molecules, and double-stranded DNAs are present, which are calculated by MD simulations.

The positions at which nanowires (solid substance) and water were present were determined on the basis of the results of the MD simulation. The nanowires had a length of about 2 μm. As is illustrated in FIG. 11, water was distributed in a large amount in the surface layer-portion (region that is a little less than 2 μm from the surface) of the nanowires and formed a layer having a high density between low-density layers. Subsequently, DNA density distribution was calculated by MD simulation. FIG. 12 illustrates the density distribution of single-stranded DNAs, while FIG. 13 illustrates the density distribution of double-stranded DNAs. As illustrated in FIG. 12, the single-stranded DNAs had a high-density peak at a position farther away from the first peak of water. This suggests that the single-stranded DNAs (5 mer) may interact with the nanowires with the water molecule layer being interposed therebetween. As illustrated in FIG. 13, the double-stranded DNAs (5 base pairs) had a high-density peak at a position farther from the nanowires than the single-stranded DNAs. The above data agree with the fact that double-stranded DNAs have a weaker interaction with the nanowires than single-stranded DNAs.

On the other hand, when the number of bases was large, both ssDNAs and dsDNAs interacted with the oxide nanowires in a suitable manner. The dsDNAs recognized the oxide nanowires with a large amount of phosphate backbones, thereby produced the polyvalent effects, and consequently adsorbed on the oxide nanowires in a stable manner. This clarified that the nanowires strongly interact with non-base pairing bases and strongly bind to the phosphate backbones of DNAs. Thus, it was clarified that, in the case where cfDNAs are to be extracted with the oxide nanowires, it is advantageous that the DNAs have a ssDNA portion and the DNAs be long.

The present disclosure provides a method for extracting a biomolecule or a biological substance (hereinafter, they are referred collectively as "biomolecule") included in a solution, the method including introducing an eluent for a target biomolecule to nanowires having the target biomolecule to elute the target biomolecule from the nanowires.

The "solution" may be a body fluid or a liquid (e.g., a diluted solution or treated solution) derived from a body fluid. The solution may be a solution other than a body fluid (solution not derived from a body fluid), an artificially prepared liquid, or a liquid mixture of a body fluid or a solution derived from a body fluid with a solution that is not derived from a body fluid. The solution may be a solution used in the measurement of samples or a solution used in the measurement for calibration. The solution may be used in the form of a stock solution or may be a liquid prepared by diluting or concentrating a stock solution. The solution may be a reference solution or a calibration solution. The sample that is to be analyzed may be an analyte. The solution may include a buffer solution, such as phosphate-buffered saline (PBS) or N-tris(hydroxymethyl)methyl-2-aminoethanesulfonic acid buffer solution (TES), which contains the substance that is to be collected. The body fluid may include an additive. As an additive, for example, a stabilizer or a pH-controlling agent may be added.

In some embodiments, the solution may be an aqueous solution. The solvent of the solution may be water. In some embodiments, the solvent of the solution may be another substance and may include a substance other than water. For example, the solvent may be ethanol.

The "body fluid" may be a solution. The body fluid may be either liquid or solid. For example, the body fluid may be frozen. The solution may, but does not necessarily, contain the substance that is to be collected, such as a biomolecule. The solution may contain a substance used for measuring the substance that is to be collected.

The body fluid may be a body fluid of an animal. The animal may be a reptile, a mammal, or an amphibian. The mammal may be a dog, a cat, cattle, a horse, a sheep, a swine, a hamster, a rat, a mouse, a squirrel, and a primate, such as a monkey, a gorilla, a chimpanzee, a bonobo, or a human.

The body fluid may be a lymph fluid; a tissue fluid, such as an interstitial fluid or an intercellular fluid; a coelomic fluid; a serous cavity fluid; a pleural effusion; ascites; pericardial effusion; a cerebrospinal fluid; a synovial fluid; or an aqueous humor. The body fluid may be a digestive juice, such as a saliva, a gastric juice, a bile, a pancreatic juice, or an intestinal juice. The body fluid may be sweat, a lacrimal fluid, a nasal secretion, urine, a seminal fluid, a vaginal secretion, an amniotic fluid, or milk.

The term "urine" refers to a liquid discharge formed in the kidneys. Urine may be either a liquid or substance discharged from the body through the urethra or a liquid or substance stored in the urinary bladder. The term "saliva" refers to a secretion secreted by the salivary gland into the oral cavity.

The body fluid may be extracted, collected, or sampled from the body using an extractor such as an injector.

The solution may be a body fluid of a healthy target, may be a body fluid of a target with a specific disease (e.g., but not limited to, lung cancer, liver cancer, pancreas cancer, bladder cancer, or prostatic cancer), and may be a body fluid of a target suspected of having a specific disease.

The term "biomolecule" used in the present specification refers generally to a biological substance. The term "biological substance" refers collectively to high-molecular-weight organic compounds that are included in living bodies and responsible for life phenomena. Examples of the biological substance include a protein, a lipid, a nucleic acid, a hormone, a sugar, and an amino acid. The biomolecule may be a complex of biomolecules, such as a protein complex or a polyprotein complex. The biomolecule may be a nucleic acid. The biomolecule may be either a vesicle or an extracellular vesicle (EV).

The substance that is to be captured, eluted, and collected (e.g., extracted or sampled; hereinafter, also referred to as "collected") is not necessarily a biomolecule and may be a non-biomolecule, and the substance may be an inorganic molecule, an organic molecule, or the like.

The biomolecule may be a deoxyribonucleic acid (DNA) and may include a DNA.

The biomolecule may be a ribonucleic acid (RNA) and may include a ribonucleic acid (RNA). Examples of the RNA include, but are not limited to, a messenger RNA (mRNA), a transfer RNA (tRNA), a ribosomal RNA (rRNA), a non-coding RNA (ncRNA), a microRNA (miRNA), a ribozyme, and a double-stranded RNA (dsRNA). The biomolecule may include two or more of the above RNAs. The above RNAs may be modified. The RNA and miRNA may be responsible for the occurrence and development of a cancer, a cardiovascular disease, a neurodegenerative disease, a psychiatric disorder, a chronic inflammatory disease, or the like. The miRNA may be an RNA that promotes a cancer or provides a positive control (onco miRNA (oncogenic miRNA or cancer-promoting miRNA)) or an RNA that suppresses a cancer or provides a negative control (Tumor Suppressor miRNA (cancer-suppressing miRNA)).

The biomolecule may be an exosome or an exosome complex. The biomolecule may be a cell organelle or a vesicle. Examples of the vesicle include, but are not limited to, a vacuole, a lysosome, a transport vesicle, a secretion, a gas vacuole, an extracellular matrix vesicle, and an extracellular vesicle. The biomolecule may include two or more of the above vesicles. Examples of the extracellular vesicle include, but are not limited to, an exosome, an exotome, a shedding microvesicle, a microvesicle, membrane particles, a protoplasmic membrane, and an apoptotic bleb. The vesicle may include a nucleic acid.

The biomolecule may be, but is not limited to, a cell and may include a cell. The cell may be an erythrocyte, a leukocyte, an immunocyte, or the like. The biomolecule may be a virus, a germ, or the like.

The biomolecule may be adsorbed on or bound onto the surfaces of the nanowires. From a microscopic viewpoint, the adsorption of a biomolecule on the surfaces of the nanowires may be fixing or a thermodynamical equilibrium state in which adsorption and desorption repeatedly occur. The equilibrium state may be represented by an association constant Ka. The expressions “capture” and “elution” by the nanowires do not always mean the state where all the biomolecules are captured or eluted and may mean an equilibrium state in which capture and elution repeatedly occur.

The term “elute” used in the present specification is used interchangeably with “elute”, “free”, “liberate”, or “separate” and refers primarily to releasing a biomolecule captured by the nanowires from the captured state. The elution may be performed under conditions suitable for elution. The term “elute” refers also to releasing a part or the entirety of the captured biomolecules from the captured state. The term “elute” may refer to releasing a part or the entirety of the captured biomolecules into a solution. The term “eluting power” used in the present specification refers to an ability of an eluent which is responsible for the speed at which the biomolecules captured by the nanowires are released into a solution, the amount of the biomolecules released into the solution, or both of the above speed and amount. The term “elution conditions” used in the present specification refers to the treatment conditions other than the composition of the solution (e.g., temperature conditions).

The term “eluent” used in the present specification refers primarily to a substance or solution that elutes biomolecules captured by the nanowires from the nanowires or that shifts the equilibrium state toward elution. The eluent functions to shift the capture-elution equilibrium state toward elution.

The term “eluent” refers to, for example, but not limited to, water, distilled water, ultrapure water (e.g., having 18.2 MΩ·cm), sterilized water, pyrogen-free water, an ethylenediaminetetraacetic acid (EDTA)-containing aqueous solution, a low-salt strength aqueous solution, a heat treatment, ethanol, or a buffer solution (e.g., phosphate-buffered saline (PBS) or N-tris(hydroxymethyl)methyl-2-aminoethanesulfonic acid buffer solution (TES)). The eluent may be, for example, but is not limited to, a buffer or solution that includes Tris-HCl, TE (Tris-EDTA; including Tris-HCl and EDTA), sodium acetate, ammonium acetate, TAE (Tris-acetate EDTA; including Tris, acetic acid, and EDTA), TBE (Tris-borate EDTA; including Tris, boric acid, and EDTA), MOPS ((3-(N-Morpholino)propanesulfonic acid), which may include potassium hydroxide for pH adjustment), SSC (Saline Sodium Citrate; including sodium citrate and sodium chloride), or the like. The eluent may include one or more active component having an eluting power. The eluent may include one or more active component having an eluting power and a solvent (e.g., water). The eluent preferably has a composition suitable for stabilizing the presence of biomolecules.

The state of equilibrium of capture of biomolecules by the nanowires can be represented by:

$$[\text{Concentration of nanowires}]\times[\text{Concentration of introduced biomolecules}]/Ka$$

Thus, in general, the use of an eluent having a relatively high binding constant Ka enables the captured biomolecules to be eluted from the nanowires in an efficient manner.

The “elution” in the present disclosure can also be performed by a method that does not include the introduction of the eluent. For example, the biomolecules can be eluted from the nanowires by performing heating.

Example: Capture of miRNAs on Nanowires and Elution Thereof

A test in which miRNA were captured on nanowires and subsequently eluted is described below.

<Production of Nanowires and Evaluation of Properties of Nanowires>

ZnO nanowires were grown on a Si substrate by a seed-assisted hydrothermal process.

A chromium (Cr) layer having a thickness of 20 nm was deposited on a Si(100) substrate (Advantech Co., Ltd.) by electron cyclotron resonance (ECR) sputtering (EIS-200ERT-YN, Elionix Inc.). The sputtering target used was a high-melting Cr-based alloy having a purity of 99.999% (Kojundo Chemical Laboratory Co., Ltd.). First, a Si(100) substrate was cut to a size of 2×4 $cm^2$. Two fluid regions (20×2 $mm^2$) were covered with a positive photoresist (OFPR8600, Tokyo Ohka Kogyo Co., Ltd.), and a microchannel pattern was formed by photolithography. Then, developing was performed with a developing solution (NMD-3.3.38%, Tokyo Ohka Kogyo Co., Ltd.).

After the Cr seed layer had been deposited, the photoresist was removed with 70° C. isopropanol using an ultrasonic device. The substrate having the seed layer was oxidized in an oven at 400° C. for 2 hours to form scaffolds for ZnO nanowires.

After preparation of the seed layer, a growth solution was prepared using 15-mM hexamethylenetetramine (HMTA). As ZnO nanowire precursors, HMTA (ACS, Thermo Fisher Scientific K. K.) and 15-mM zinc nitrate hexahydrate $Zn(NO_3)_2\cdot 6H_2O$ (Wako Pure Chemical Industries, Ltd.) were added to a 0.8-M ammonium solution (Wako Pure Chemical Industries, Ltd.) in order to markedly increase the length of the ZnO nanowires. The nanowires were grown for 3 hours in an oven at a typical growth temperature of 95° C.

<Production of Nanowire Device>

Figure 14:
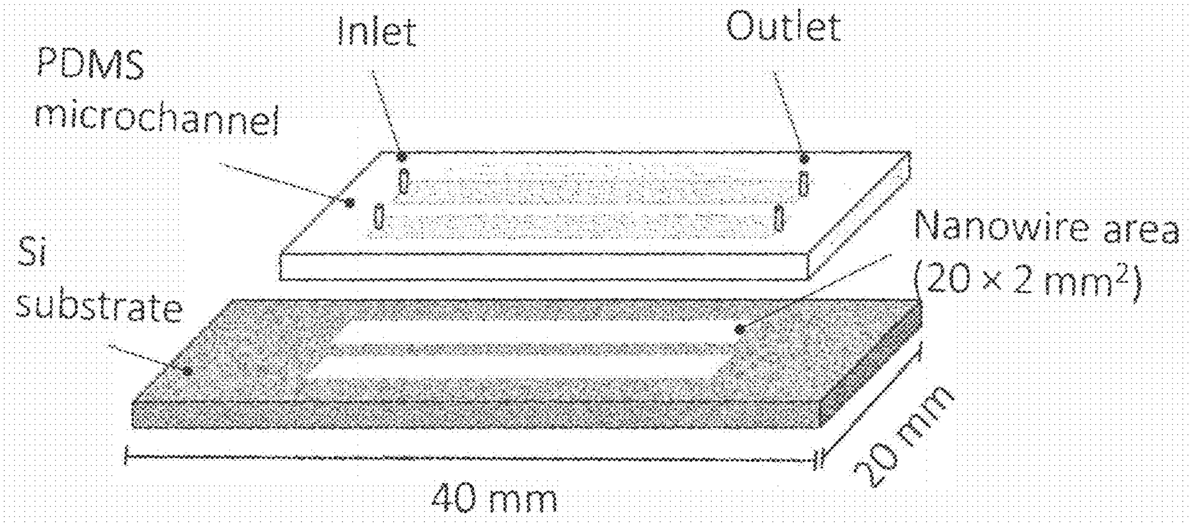
FIG. 14 is an exploded perspective view of a nanowire device according to an example.

After the production of the ZnO nanowires on the microchannel pattern, the substrate and the nanowires were cleaned with deionized water and then dried in a nitrogen gas stream. The dried substrate was treated with oxygen plasma, and poly(dimethylsiloxane) (PDMS) having a depth of 30 μm was attached thereto. PDMS (SILPOT 184, produced by Dow Corning Corp.) was patterned to have microchannels and 0.05 mm inlet and outlet holes (FIG. 14).

Using a capillary tube (ICT-55, Institute of Microchemical Technology Co., Ltd.), the microchannels were connected to a microliter syringe (Hamilton Company, not illustrated in the drawings) for sample introduction.

<Capture and Elution of EVs by Nanowire Device>

Figure 15:
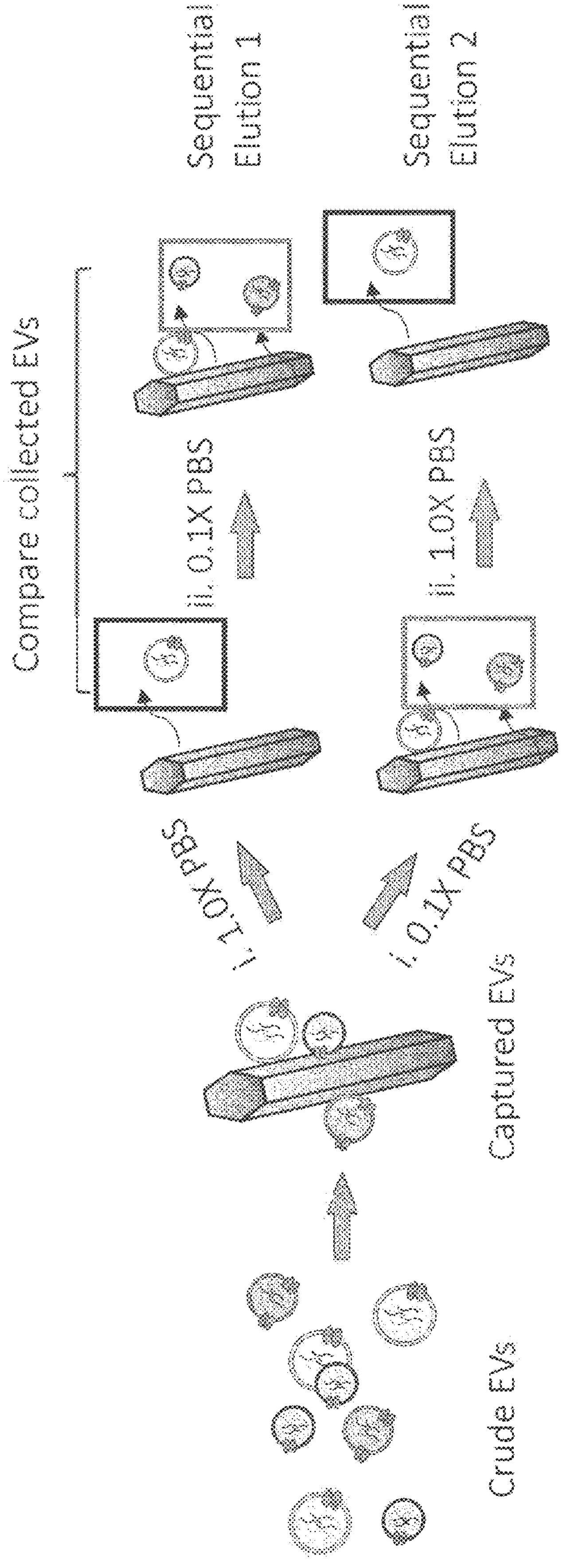
FIG. 15 illustrates the process of capture and elution of EVs using nanowires according to an example.

The nanowire device was attached to a dual-channel syringe pump (Fusion 100, Chemyx Inc.). An EV sample collected from a MDA-MB-231 culture medium was injected into the device consistently at a flow rate of 10 μL/min. Then, 250 μL of EV-suspended PBS was fed to the microfluid nanowire device to capture the EVs on each nanowire (FIG. 15).

Subsequently, 250 μL of a buffer was introduced to the device at a flow rate of 10 μL/min using a specific one of the PBS solutions having different concentrations in order to release the EVs captured on the nanowires. Specifically, in the elution sequence 1, 250 μL of 1.0×PBS was first introduced and, subsequently, 250 μL of 0.1×PBS was introduced. Conversely, in the elution sequence 2, 250 μL of 0.1×PBS was first introduced and, subsequently, 250 μL of 1.0×PBS was introduced (FIG. 15).

The solution was collected at four timings below, and the EVs included in each solution were analyzed:

a) The EVs included in the stock solution, that is, the solution that had not been introduced to the nanowire device ("Crude EVs");
b) The EVs included in the solution that had been passed through the nanowire device, that is, the solution that included EVs that were not captured by the nanowire device ("Uncaptured EV");
c) The EVs eluted with 1.0×PBS after being captured by the nanowires ("Released EVs (1.0×PBS)"); and
d) The EVs eluted with 0.1×PBS after being captured by the nanowires ("Released EVs (0.1×PBS)").

<Test Result 1: Elution Sequence Vs Number of Eluted Particles>

Figure 16A:
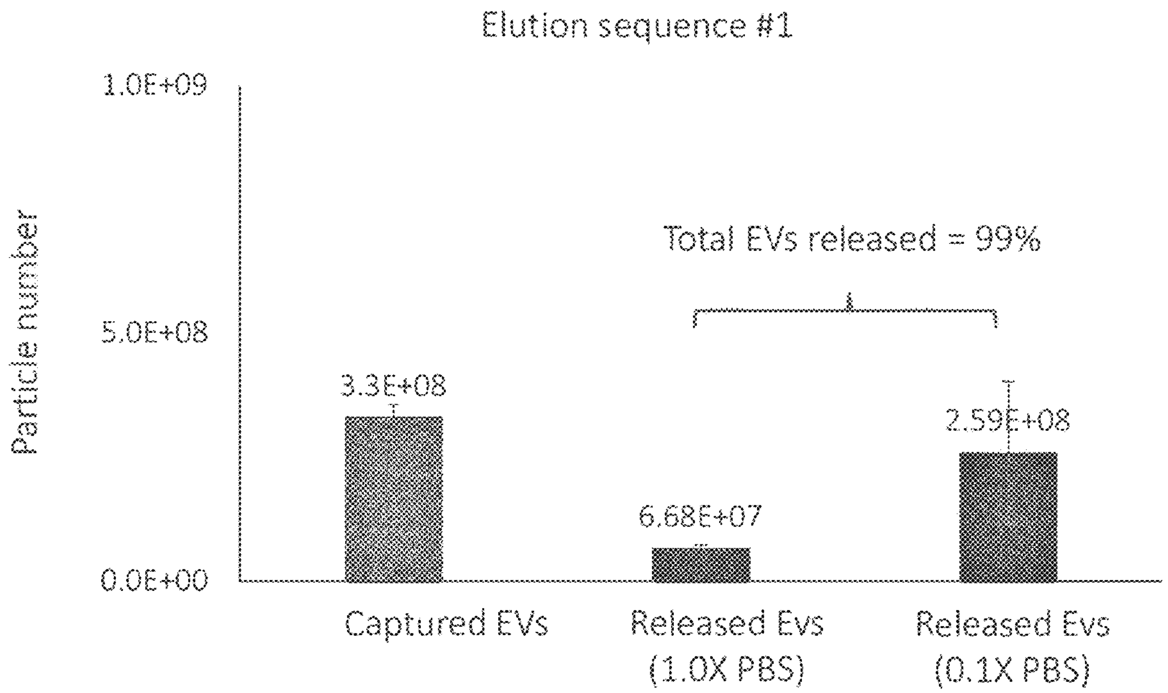
FIG. 16A is a graph providing a comparison between the number of particles that correspond to "Released EV", "Released EVs", and "Captured EVs" in the elution sequence 1.
Figure 16B:
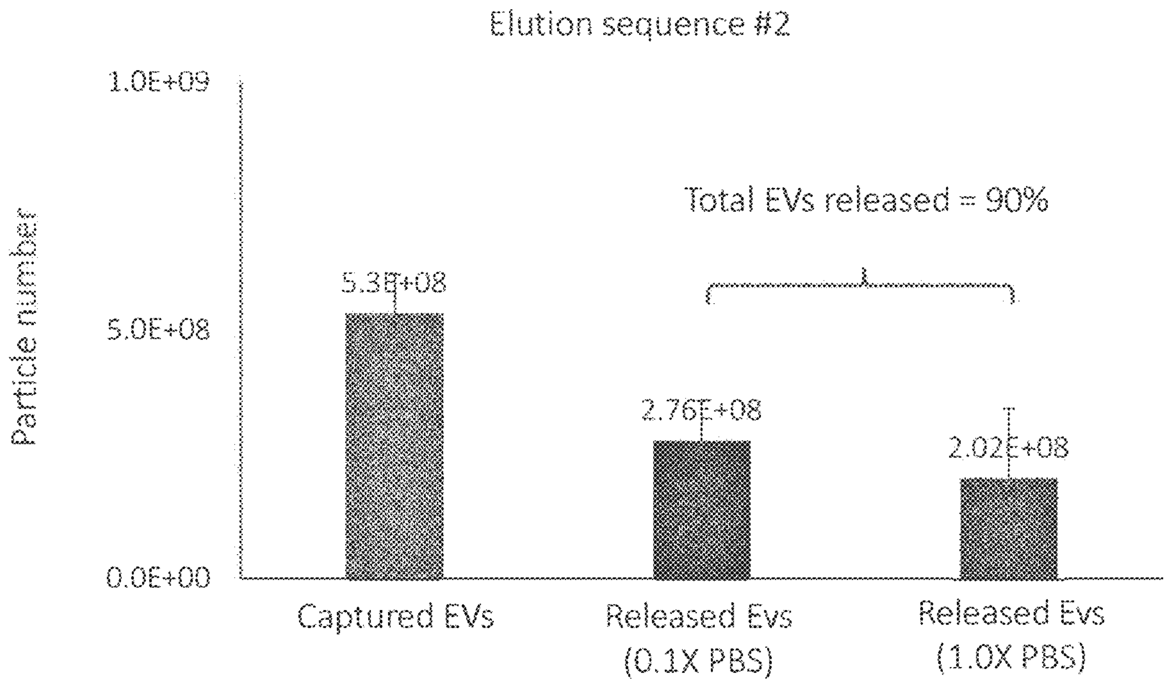
FIG. 16B is a graph providing a comparison between the number of particles that correspond to "Released EV", "Released EVs", and "Captured EVs" in the elution sequence 2.

FIG. 16-1 illustrates the number of the EVs obtained by introduction of 1.0×PBS (Released EVs (1.0×PBS)), the number of the EVs obtained subsequently by introduction of 0.1×PBS (Released EVs (0.1×PBS)), and the total of the two numbers (Captured EVs) in the elution sequence 1. FIG. 16-2 illustrates the number of the EVs obtained by introduction of 0.1×PBS (Released EVs (0.1×PBS)), the number of the EVs obtained subsequently by introduction of 1.0×PBS (Released EVs (1.0×PBS)), and the total of the two numbers (Captured EVs) in the elution sequence 2.

In the elution sequence 2, the 0.1×PBS and the 1.0×PBS eluted substantially the same number of EVs. On the other hand, in the elution sequence 1, the number of EV particles obtained by the first 1.0×PBS was clearly smaller than the number of EVs obtained by the subsequent 0.1×PBS.

The above results suggest that the number of EV particles eluted from the nanowires can be controlled by changing the elution sequence and other elution conditions, such as the concentration of PBS, that is, the type of the eluent, and conditions.

<Surface Biomarker Analysis by ExoView>

In order to determine the surface biomarker properties of each isolated EV subgroup, single particle interferometric reflectance imaging sensing (SP-IRIS) by ExoView platform (ExoView R100, NanoView Biosciences) was used. For 108 to 109 particles of EV samples, the concentration of the sample was optimized. It was not necessary to dilute the 108 particles. Among the 109 particles, 1:1 was diluted. In order to prevent the supersaturation of the chip, the incubation solution attached to the ExoView kit was used. ExoView plasma tetraspanin kit was used. An analysis was conducted using CD63, CD81, and CD9 as detection antibodies and anti-CD63, anti-CD81, and anti-CD9 as capture antibodies. The diluted EVs were loaded on the ExoView chip. A protein film analysis was conducted in accordance with instructions given by the maker. AF647, AF555, and AF488 were used as second antibodies for fluorescent imaging.

The four EV subgroups below were analyzed; a) The EVs included in the stock solution, that is, the solution that had not been introduced to the nanowire device ("Crude EVs"), b) The EVs included in the solution that had been passed through the nanowire device, that is, the solution that included EVs that were not captured by the nanowire device ("Uncaptured EV"), c) The EVs eluted with 1.0×PBS after being captured by the nanowires ("Released EVs (1.0×PBS)"), and d) The EVs eluted with 0.1×PBS after being captured by the nanowires ("Released EVs (0.1×PBS)").

<Test Results 2: Eluent Concentration vs EV Properties>

Figure 17:
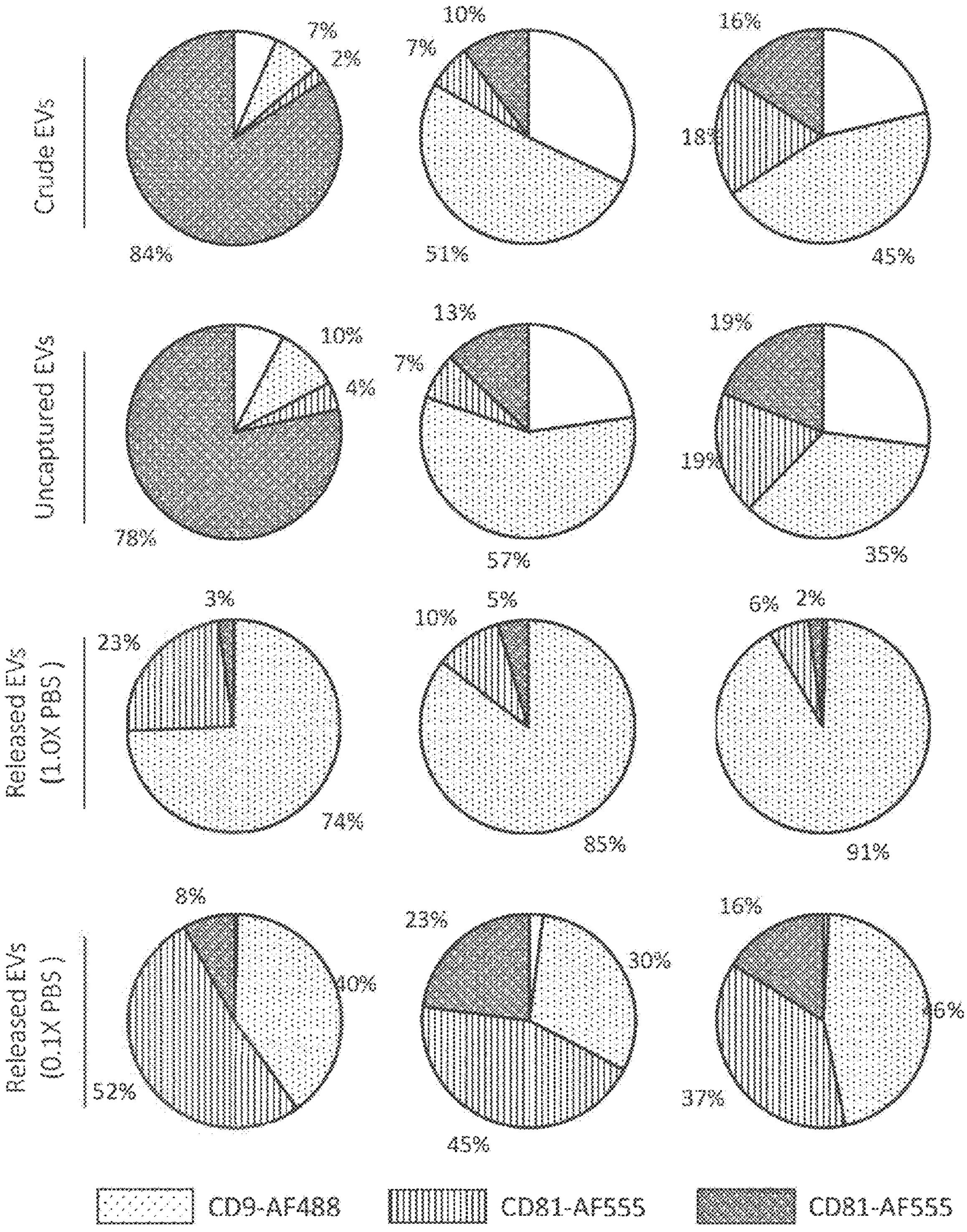
FIG. 17 illustrates the results of colocalization analysis which represent phenotypic markers for antibodies captured by EV subgroups.

EVs were captured by nanowires as in Test result 1. Subsequently, elution was performed by first introducing 1.0×PBS and subsequently introducing 0.1×PBS. FIG. 17 illustrates the coexpression of three tetraspanins (CD63, CD81, and CD9) for each of the four EV subgroups described above. In a) Crude EVs and b) Uncaptured EVs, antigens at which CD63, CD81, and CD9 target were captured. On the other hand, in c) Released EVs (1.0×PBS) and d) Released EVs (0.1×PBS), completely different results were obtained. That is, regardless of the type of CD63, CD81, and CD9, CD9 was most dominantly detected in c) and CD81 and CD9 were detected with substantially the same intensity in d). The above results suggest that it is possible to selectively elute a specific type of EVs, that is, in this case, a specific type of antigen expressed in the membrane protein of EVs, from the nanowires depending on the concentration of PBS.

The above results suggest that it is possible to control the type of EVs eluted from the nanowires (e.g., surface electric charge or type of antigen expressed in the membrane protein) by changing the elution sequence and other elution conditions, such as the concentration of PBS, that is, the type of the eluent, and conditions.

Other Example: Elution Control by Heat

In some embodiments, a plurality of types of biomolecules captured by the nanowires may be eluted individually by changing heat conditions. For example, a solution containing miRNAs and EVs is introduced to a nanowire device, and both of the above biomolecules are captured by the nanowires. Subsequently, when heating is performed at 95° C., miRNAs become eluted from the nanowires. As a result, free miRNAs can be collected from the nanowire device. Note that the EVs do not elute in the above treatment. Subsequently, a lysis buffer is introduced to the nanowires to disrupt the EVs. This enables the biomolecules included in the EVs, such as miRNAs, to be liberated. Thus, miRNAs included in the EVs can be collected. As described above, from a solution derived from the same living body, free miRNAs and miRNAs included in the EVs can be collected separately.

The present disclosure includes the following embodiments:

A001

A method for extracting a biomolecule included in a solution, the method including:

providing a nanowire;

introducing a solution including a target biomolecule to the nanowire to capture the target biomolecule; and introducing an eluent for the target biomolecule to the nanowire having the target biomolecule to elute the target biomolecule from the nanowire.

A001b

A method for extracting a biomolecule included in a solution, the method including:

introducing a solution including a target biomolecule to a nanowire to capture the target biomolecule; and introducing an eluent for the target biomolecule to the nanowire having the target biomolecule to elute the target biomolecule from the nanowire.

A001c

A method for extracting a biomolecule included in a solution, the method including:

providing a nanowire having a target biomolecule; and introducing an eluent for the target biomolecule to the nanowire having the target biomolecule to elute the target biomolecule from the nanowire.

A001d

The method according to any one of embodiments A001 to A001c, wherein the introducing an eluent for the target biomolecule to the nanowire to elute the target biomolecule from the nanowire includes treating the nanowire having the target biomolecule under a first elution condition to elute a first target biomolecule from the nanowire; and treating the nanowire having the target biomolecule under a second elution condition different from the first elution condition to elute a second target biomolecule from the nanowire.

A001e

A method for extracting a biomolecule included in a solution, the method including:

providing a nanowire;

introducing a solution including a target biomolecule to the nanowire to capture the target biomolecule;

treating the nanowire having the target biomolecule under a first elution condition to elute a first target biomolecule from the nanowire; and treating the nanowire having the target biomolecule under a second elution condition different from the first elution condition to elute a second target biomolecule from the nanowire.

A021

A method for extracting a biomolecule included in a solution, the method including:

providing a nanowire;

introducing a solution including a target biomolecule to the nanowire to capture the target biomolecule;

introducing a first eluent having a first eluting power to a portion of the nanowire having the target biomolecule to elute a first target biomolecule from the nanowire; and introducing a second eluent having a second eluting power different from the first eluting power to another portion of the nanowire having the target biomolecule to elute a second target biomolecule from the nanowire.

A022

A method for extracting a biomolecule included in a solution, the method including:

providing a nanowire;

introducing a solution including a target biomolecule to the nanowire to capture the target biomolecule;

introducing a first eluent having a first eluting power to the nanowire having the target biomolecule to elute a first target biomolecule from the nanowire; and after the target biomolecule has been eluted from the nanowire with the first eluent, introducing a second eluent having a second eluting power different from the first eluting power to the nanowire having the target biomolecule to elute a second target biomolecule from the nanowire.

A031

The method according to Embodiment A021 or A022, wherein the first and second eluents are liberating agents of the same type but having different concentrations.

A032

The method according to Embodiment A031, wherein the first and second eluents are phosphate-buffered saline (PBS).

A041

A method for extracting a biomolecule included in a solution, the method including:

providing a nanowire;

introducing a solution including a target biomolecule to the nanowire to capture the target biomolecule;

heating the nanowire having the target biomolecule to elute a first target biomolecule from the nanowire; and introducing an eluent to the nanowire having the target biomolecule to elute a second target biomolecule from the nanowire.

A042

A method for extracting a miRNA included in a solution, the method including: providing a nanowire;

introducing a solution including a free miRNA and an EV to the nanowire to capture the free miRNA and the EV;

heating the nanowire to elute the free miRNA from the nanowire; and introducing an EV disruption solution to the nanowire to disrupt the EV and elute a miRNA included in the EV from the nanowire.

A043

The method according to embodiment A042, wherein the heating is performed at 80° C. or more, 85° C. or more, 90° C. or more, or 95° C. or more, for example, 95° C.

A044

The method according to embodiment A042 or A043, wherein the EV disruption solution is a lysis buffer.

A051

The method according to any one of embodiments A001 to A044, wherein the solution is a body fluid or a solution derived from a body fluid.

A052

The method according to embodiment A051, wherein the body fluid is urine.

A053

The method according to any one of embodiments A001 to A052, wherein the biomolecule is at least one of an EV and a nucleic acid.

A054

The method according to embodiment A053, wherein the nucleic acid is an RNA or includes an RNA.

A055

The method according to embodiment A054, wherein the RNA is a miRNA or includes a miRNA.

A061

The method according to any one of embodiments A001 to A052, wherein the nanowire or at least a surface of the nanowire is composed of an oxide selected from the group consisting of zinc oxide, aluminum oxide, titanium oxide, and silicon oxide.

Some embodiments and examples of the present disclosure have been described below. It should be noted that the embodiments and examples above are illustrative of the present disclosure. For example, each of the embodiments has been described in detail in order to explain the present disclosure in a way easy to understand. Dimensions, structures, materials, and circuits may be added and changed as needed. Embodiments obtained by combining one or a plurality of the above-described features of the present disclosure with one another are also within the scope of the present disclosure. The claims cover various modifications of the embodiments without departing from the technical ideas of the present disclosure. Thus, it should be understood that embodiments and examples disclosed in the present specification are merely illustrative and not restrictive of the scope of the present disclosure.

The invention claimed is:

1. A method for extracting a biomolecule included in a solution, the method comprising:

introducing a solution including a first and a second target biomolecules to a nanowire to capture the first and the second target biomolecules;

treating the nanowire under a first elution condition to elute the first target biomolecule from the nanowire; and treating the nanowire under a second elution condition different from the first elution condition to elute the second target biomolecule from the nanowire wherein the first and second elution conditions are selected to maximize collection of captured biomolecules.

2. The method according to claim 1, wherein the nanowire or at least a surface of the nanowire is composed of an oxide selected from the group consisting of zinc oxide, aluminum oxide, titanium oxide, and silicon oxide.

3. The method according to claim 1, wherein the eluting of the first target biomolecule from the nanowire includes introducing a first eluent having a first eluting power to the nanowire, and wherein the eluting of the second target biomolecule from the nanowire includes introducing a second eluent having a second eluting power different from the first eluting power to the nanowire.

4. The method according to claim 3, wherein the first and second eluents are liberating agents of the same type but having different concentrations.

5. The method according to claim 4, wherein the first and second eluents are phosphate-buffered saline (PBS).

6. The method according to claim 1, wherein the eluting of the first target biomolecule from the nanowire includes heating the nanowire, and wherein the eluting of the second target biomolecule from the nanowire includes introducing an eluent to the nanowire.

7. The method according to claim 1, wherein the biomolecule is at least one two of an extracellular vesicle (EV), a nucleic acid included in an EV, and a cell-free nucleic acid.

8. The method according to claim 7, wherein the nucleic acid is a DNA and/or RNA.

9. The method according to claim 8, wherein the RNA is a miRNA.

10. The method according to claim 9, wherein the first target biomolecule is a cell-free nucleic acid, wherein the second target biomolecule is a nucleic acid included in an EV, wherein the introducing of the solution including the first and the second target biomolecules to a nanowire to capture the first and second target biomolecules includes introducing a solution including the cell-free nucleic acid and the nucleic acid included in the EV, wherein the treating of the nanowire under the first elution condition includes heating the nanowire to elute the cell-free nucleic acid, and wherein the treating of the nanowire under the second elution condition includes introducing an EV disruption solution to disrupt the EV and elute the nucleic acid included in the EV.

11. The method according to claim 10, wherein after the treating of the nanowire under the first elution condition, the treating of the nanowire under the second elution condition is performed.

12. The method according to claim 10, wherein the heating is performed at 95° C.

13. The method according to claim 10, wherein the EV disruption solution is a lysis buffer.

14. The method according to claim 10, wherein the solution is a body fluid or a solution derived from a body fluid.

15. The method according to claim 14, wherein the body fluid is urine.

* * * * *